(12) United States Patent
Darekar et al.

(10) Patent No.: US 12,426,910 B2
(45) Date of Patent: Sep. 30, 2025

(54) IN-SITU FENESTRATION DEVICES WITH ULTRASONIC CUTTER

(71) Applicant: Medtronic Vascular, Inc., Santa Rosa, CA (US)

(72) Inventors: Yogesh A. Darekar, Santa Rosa, CA (US); Amal Elgamil, Santa Rosa, CA (US); Christina E. Franke, Santa Rosa, CA (US); Kevin M. Mauch, Santa Rosa, CA (US); Anish S. Nigade, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 202 days.

(21) Appl. No.: 18/368,408

(22) Filed: Sep. 14, 2023

(65) Prior Publication Data

US 2024/0081853 A1 Mar. 14, 2024

Related U.S. Application Data

(60) Provisional application No. 63/406,553, filed on Sep. 14, 2022.

(51) Int. Cl.
*A61B 17/32* (2006.01)
*A61B 17/22* (2006.01)
*A61F 2/06* (2013.01)
*A61F 2/07* (2013.01)

(52) U.S. Cl.
CPC ........... *A61B 17/320068* (2013.01); *A61B 17/22032* (2013.01); *A61B 17/320016* (2013.01); *A61F 2/07* (2013.01); *A61B 2017/22035* (2013.01); *A61B 2017/320072* (2013.01); *A61F 2002/061* (2013.01)

(58) Field of Classification Search
None
See application file for complete search history.

(56) References Cited

U.S. PATENT DOCUMENTS

| | | | |
|---|---|---|---|
| 6,866,670 B2 | 3/2005 | Rabiner et al. | |
| 7,963,960 B2 | 6/2011 | Bruszewski et al. | |
| 8,100,960 B2 | 1/2012 | Bruszewski | |
| 8,197,475 B2 | 6/2012 | Bruszewski et al. | |
| 8,292,885 B2 | 10/2012 | Bruszewski et al. | |
| 2009/0228020 A1* | 9/2009 | Wallace | A61B 34/30 606/130 |
| 2017/0086997 A1* | 3/2017 | Berg | A61F 2/954 |
| 2020/0121363 A1* | 4/2020 | Fu | A61B 17/3478 |

(Continued)

OTHER PUBLICATIONS

Hong, Y. et al., "A strongly adhesive hemostatic hydrogel for the repair of arterial and heart bleeds" Nature Communications, vol. 10, No. 2060, 2019, pp. 1-11, DOI: 10.1038/s41467-019-10004-7.

(Continued)

*Primary Examiner* — Shaun L David
(74) *Attorney, Agent, or Firm* — Brooks Kushman P.C.

(57) ABSTRACT

An in-situ fenestration device. The device includes a sheath, a sonic catheter extending with the sheath and having a cutting tool at a distal section thereof, and a balloon catheter extending within the sonic catheter. The cutting tool of the sonic catheter is configured to cut a fenestration in a graft material at a fenestration site of a stent graft upon being energized with ultrasonic energy at a cutting frequency.

20 Claims, 38 Drawing Sheets

(56) References Cited

U.S. PATENT DOCUMENTS

| | | |
|---|---|---|
| 2021/0128185 A1 | 5/2021 | Nguyen et al. |
| 2022/0079739 A1* | 3/2022 | Zhao .................. A61F 2/962 |
| 2023/0248506 A1* | 8/2023 | Zhang .................. A61F 2/07 |
| | | 623/1.13 |
| 2024/0000592 A1* | 1/2024 | Dillon .................. A61F 2/07 |
| 2024/0033027 A1* | 2/2024 | Perkins ................ A61B 34/73 |

OTHER PUBLICATIONS

Lin, J. et al., "Laser Fenestration of Aortic Stent-Grafts Followed by Noncompliant vs Cutting Balloon Dilation: A Scanning Electron Microscopy Study," Journal of Endovascular Therapy, vol. 25, No. 3, 2018, pp. 397-407 DOI: 10.1177/1526602818772311.

Smorenburg, S. P.M. et al., "Anatomic Suitability for Branched Thoracic Endovascular Repair in Patients with Aortic Arch Pathological Features," Journal of the American Heart Association, vol. 9, No. 20, 2020, pp. 1-10, DOI: 10.1161/JAHA.120.016695.

* cited by examiner

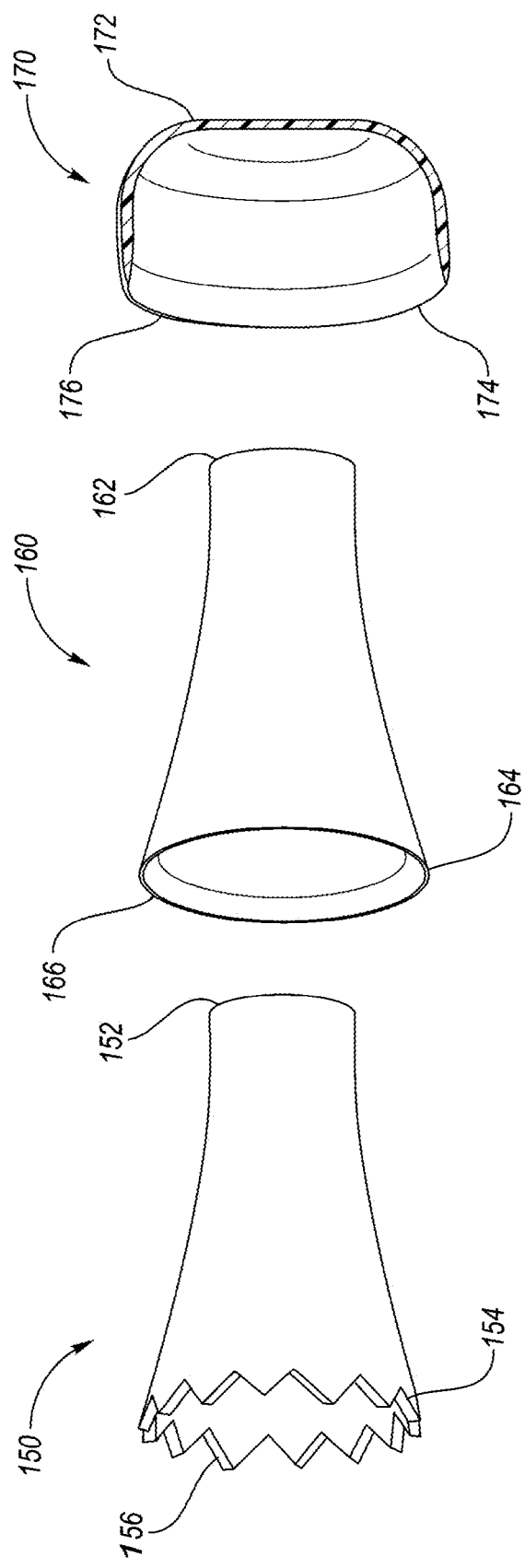

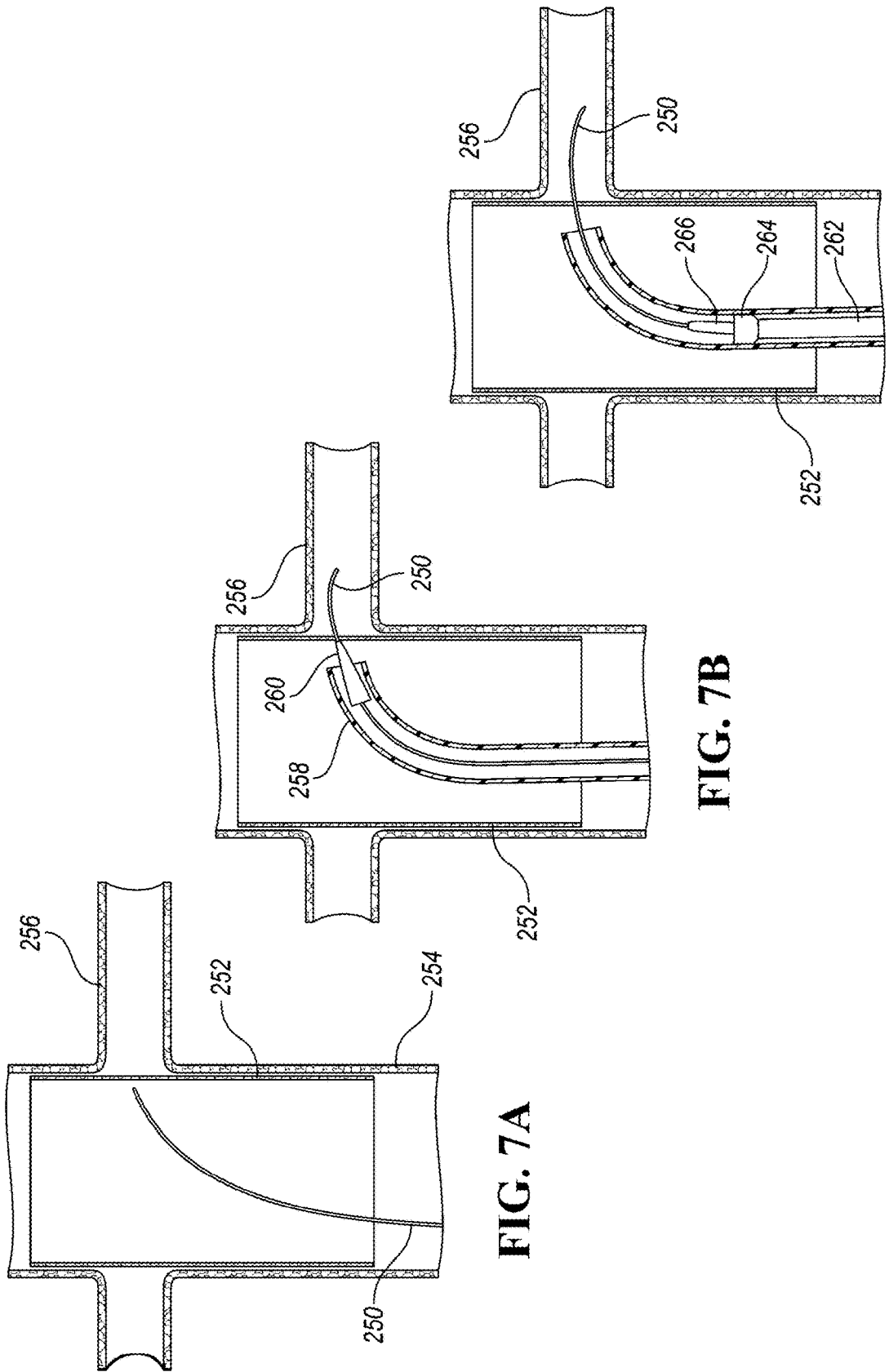

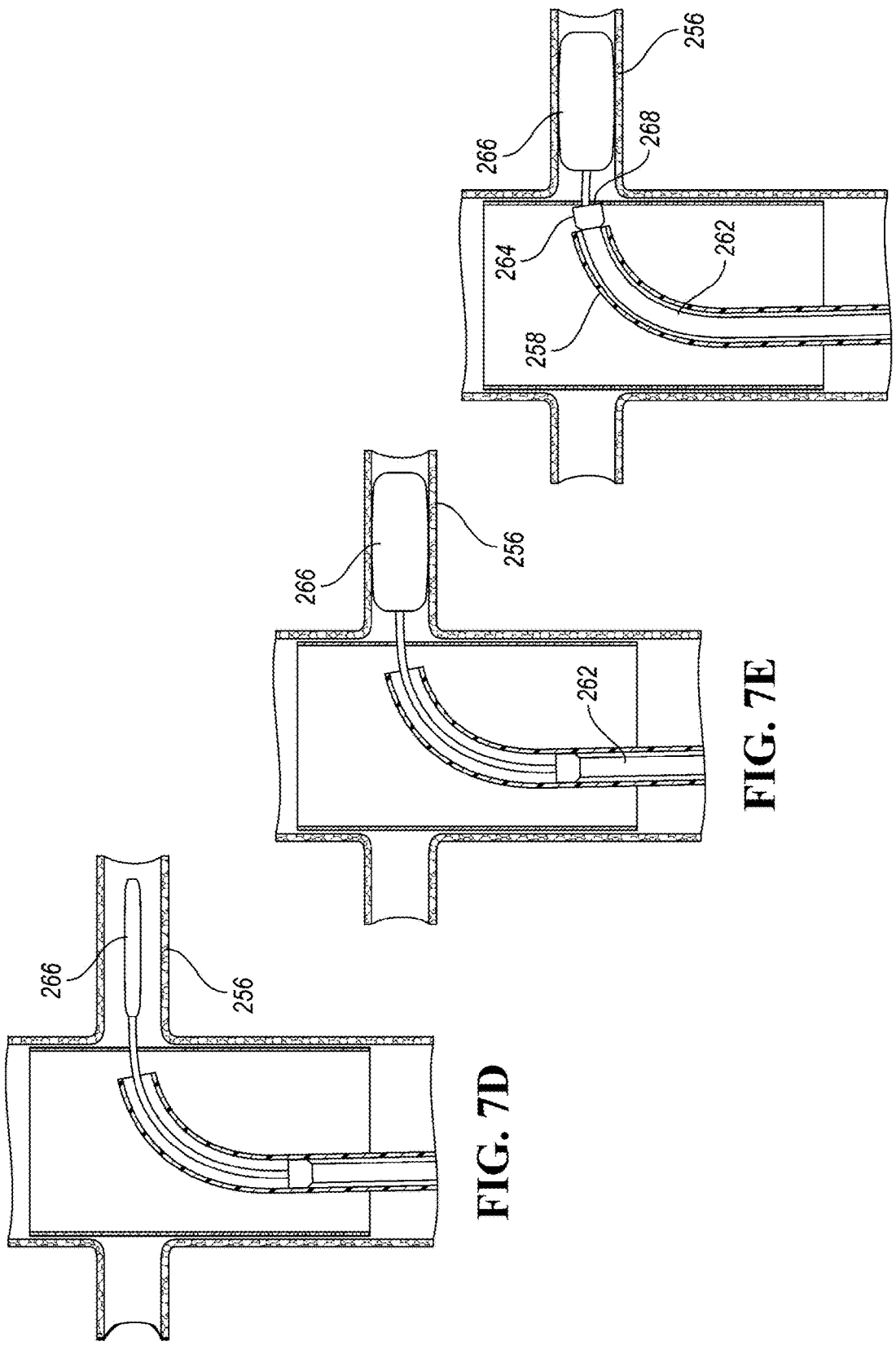

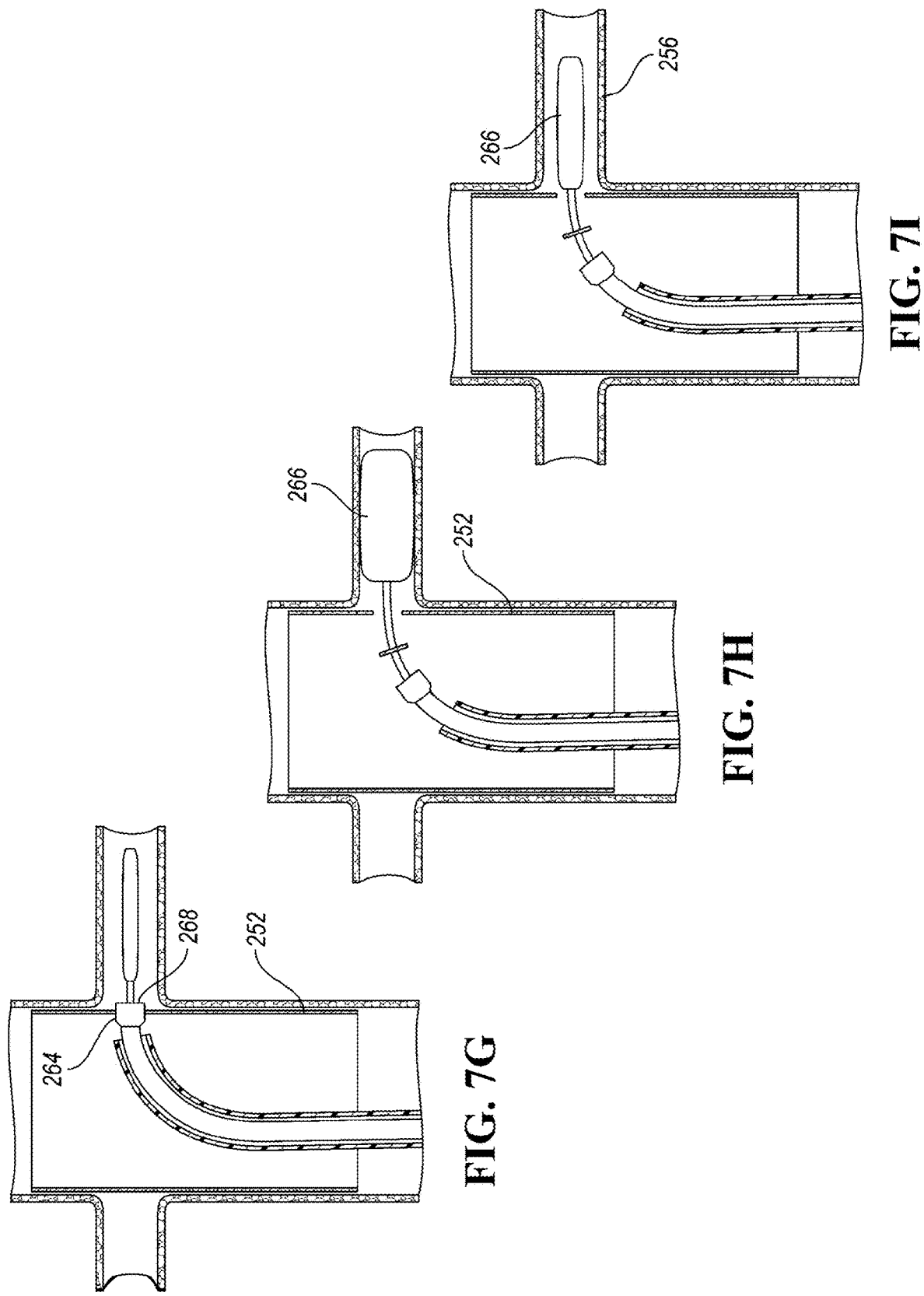

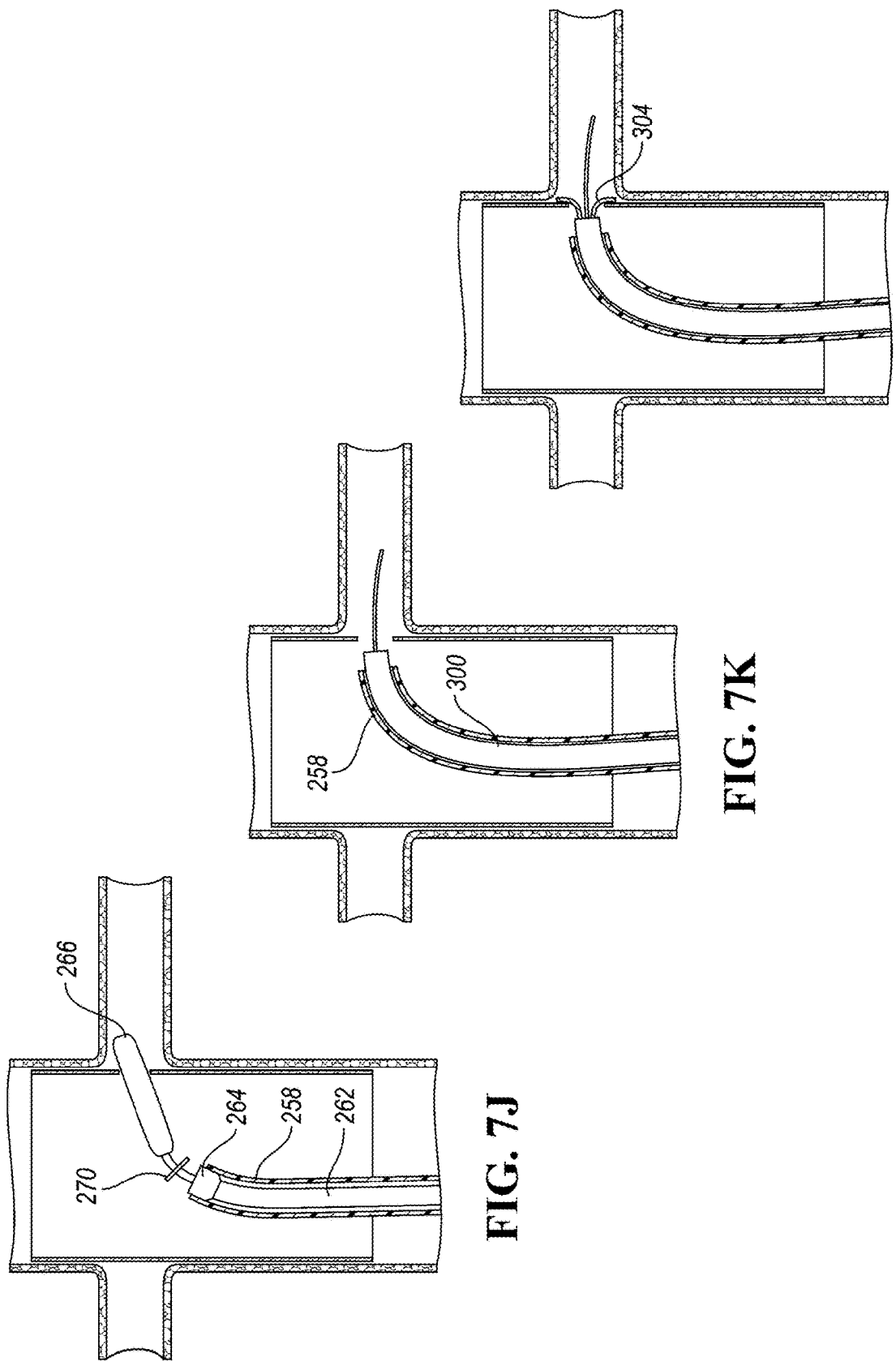

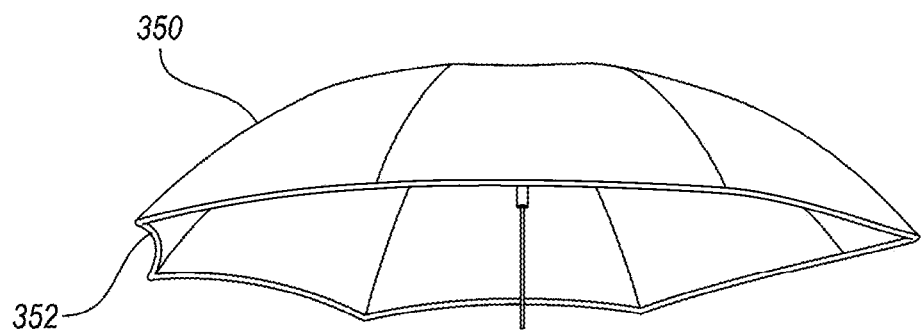
FIG. 9A
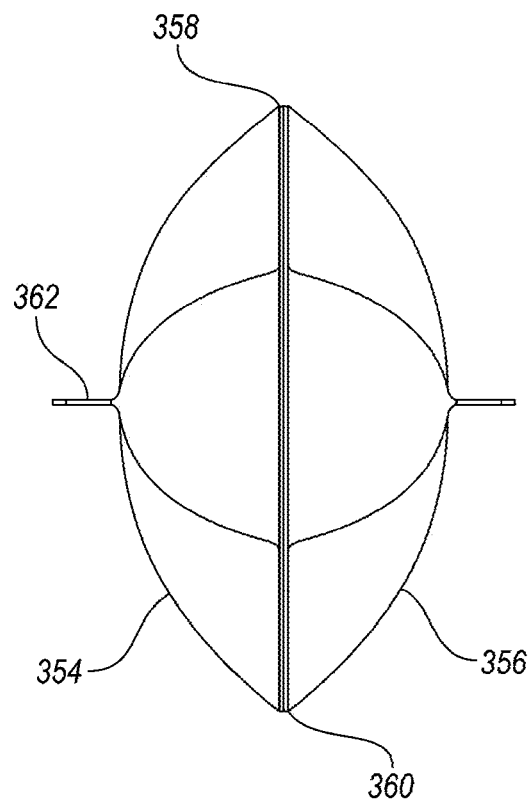 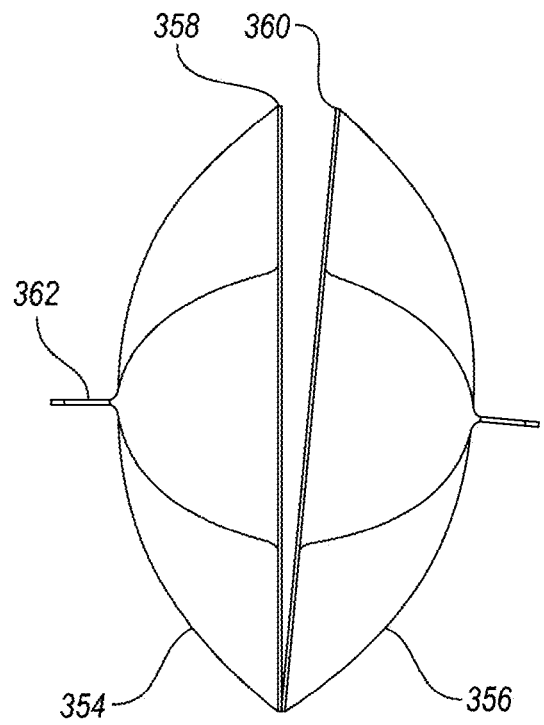
FIG. 9B  FIG. 9C

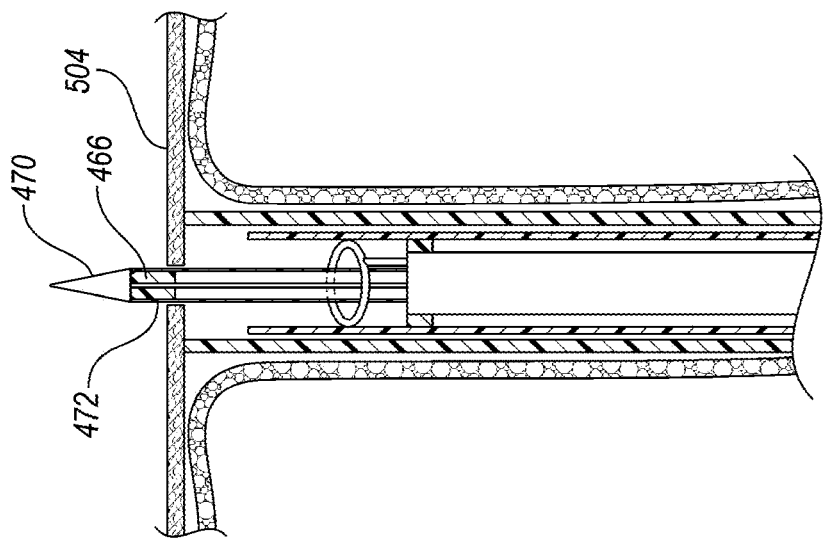
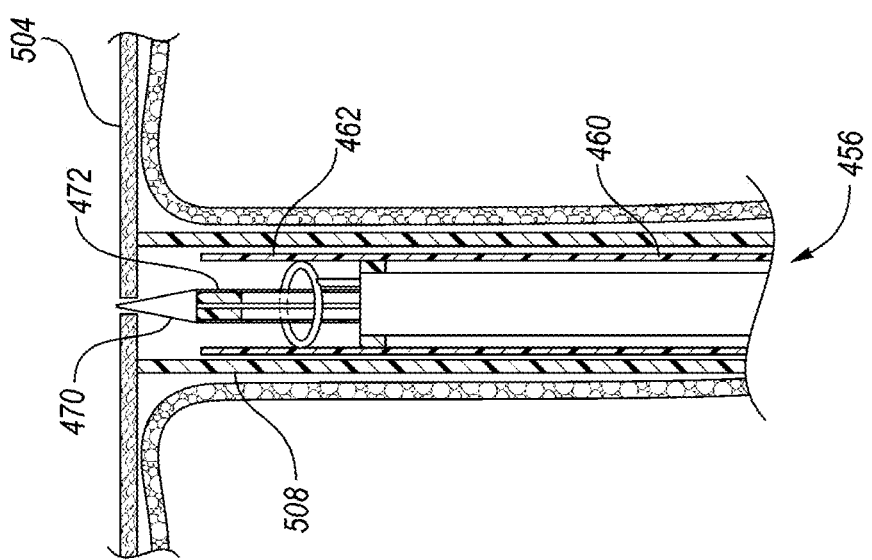

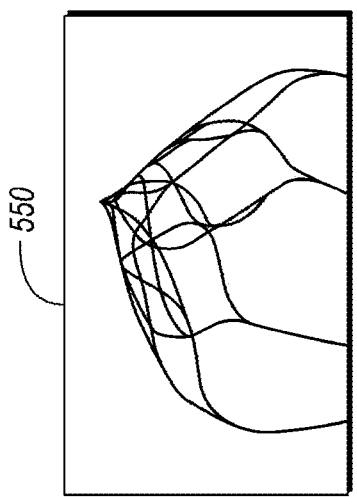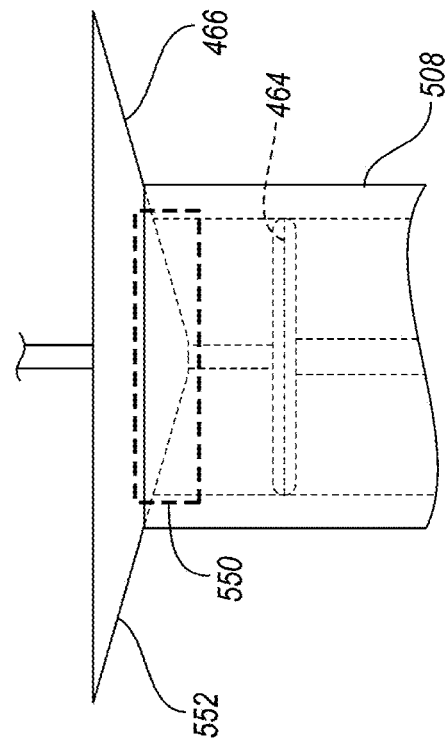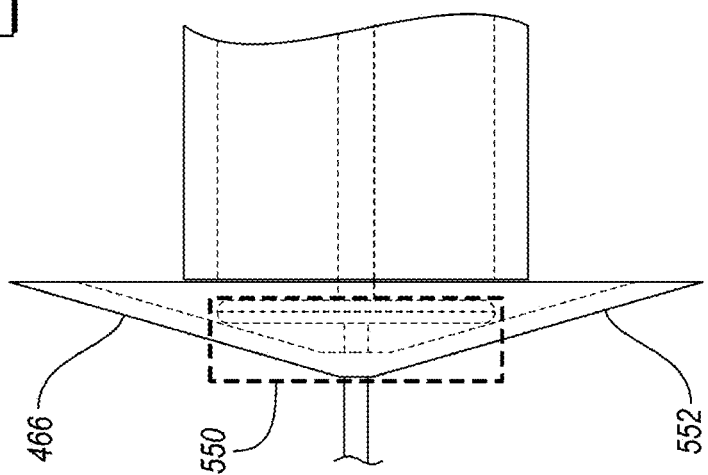
FIG. 17B
FIG. 17C
FIG. 17A

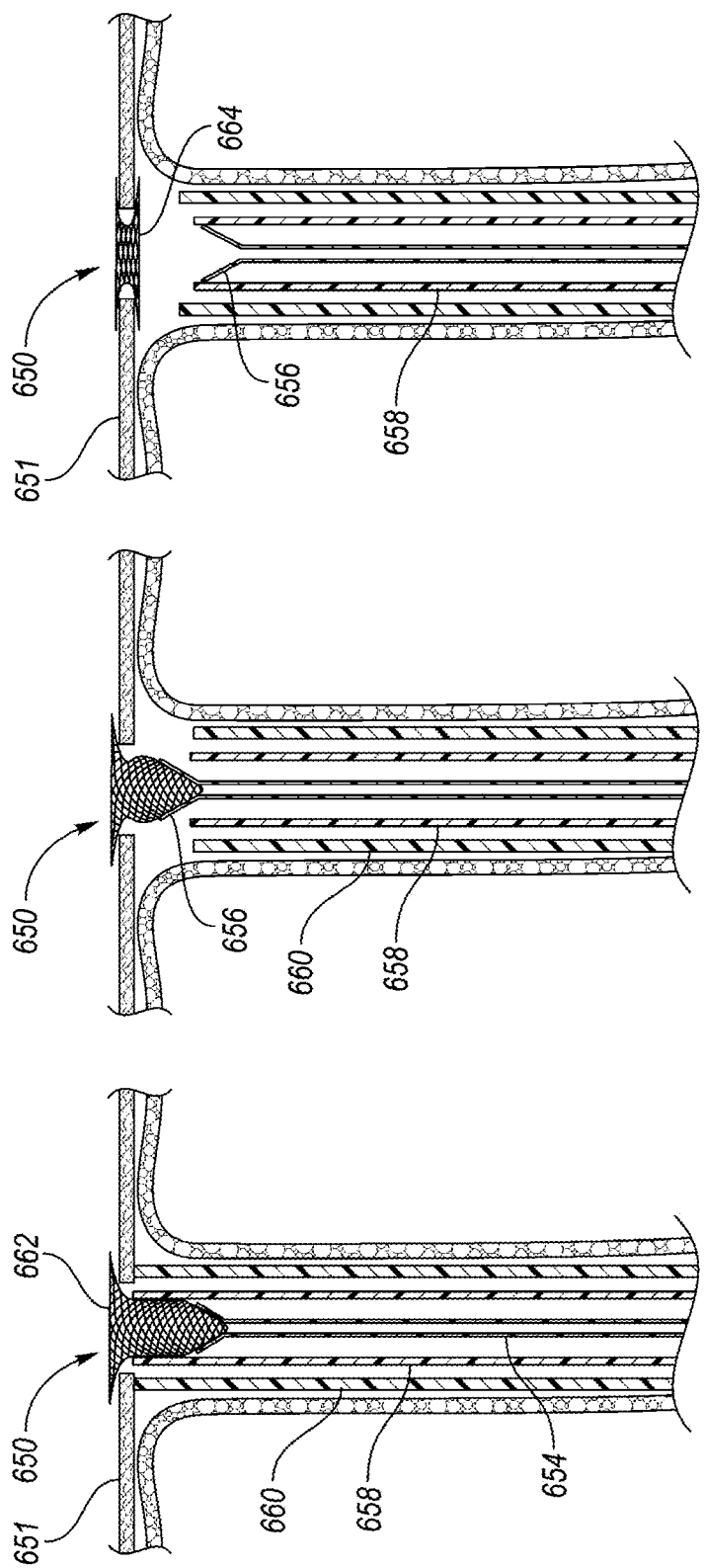

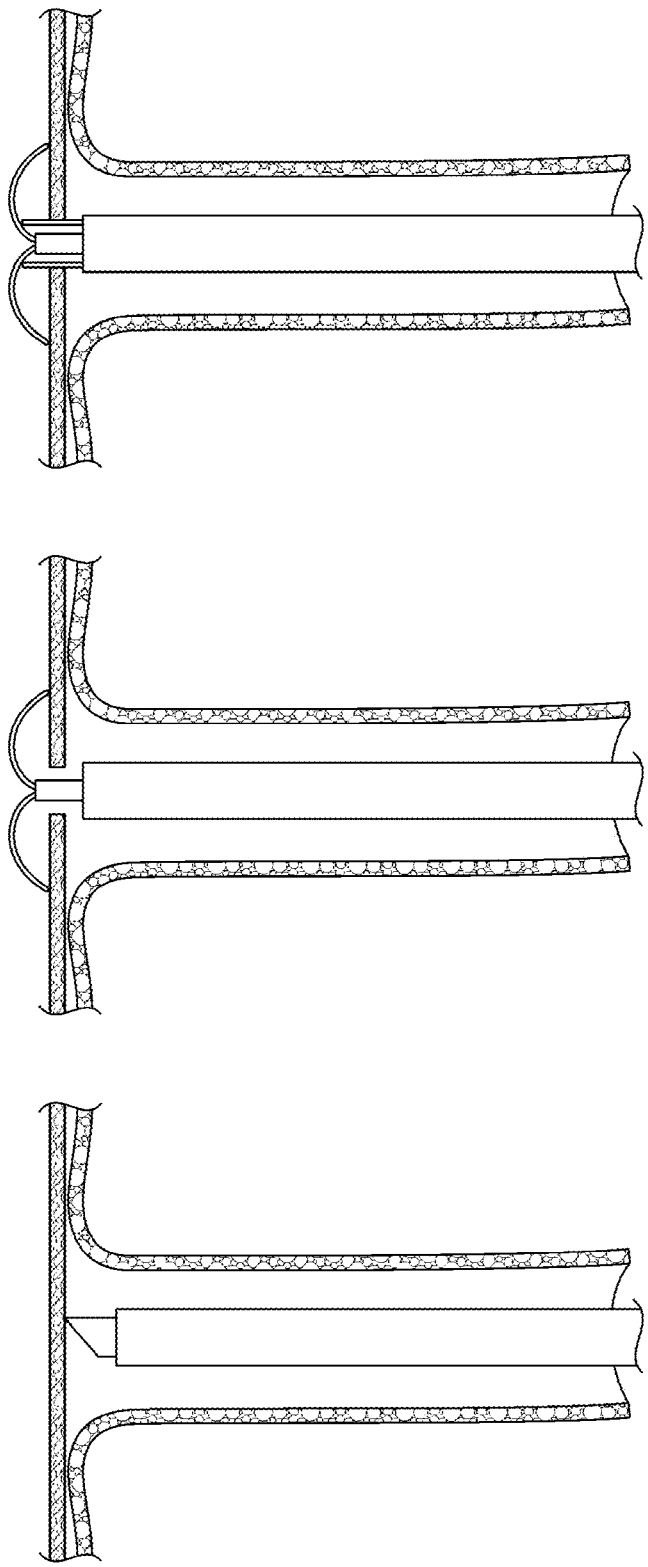

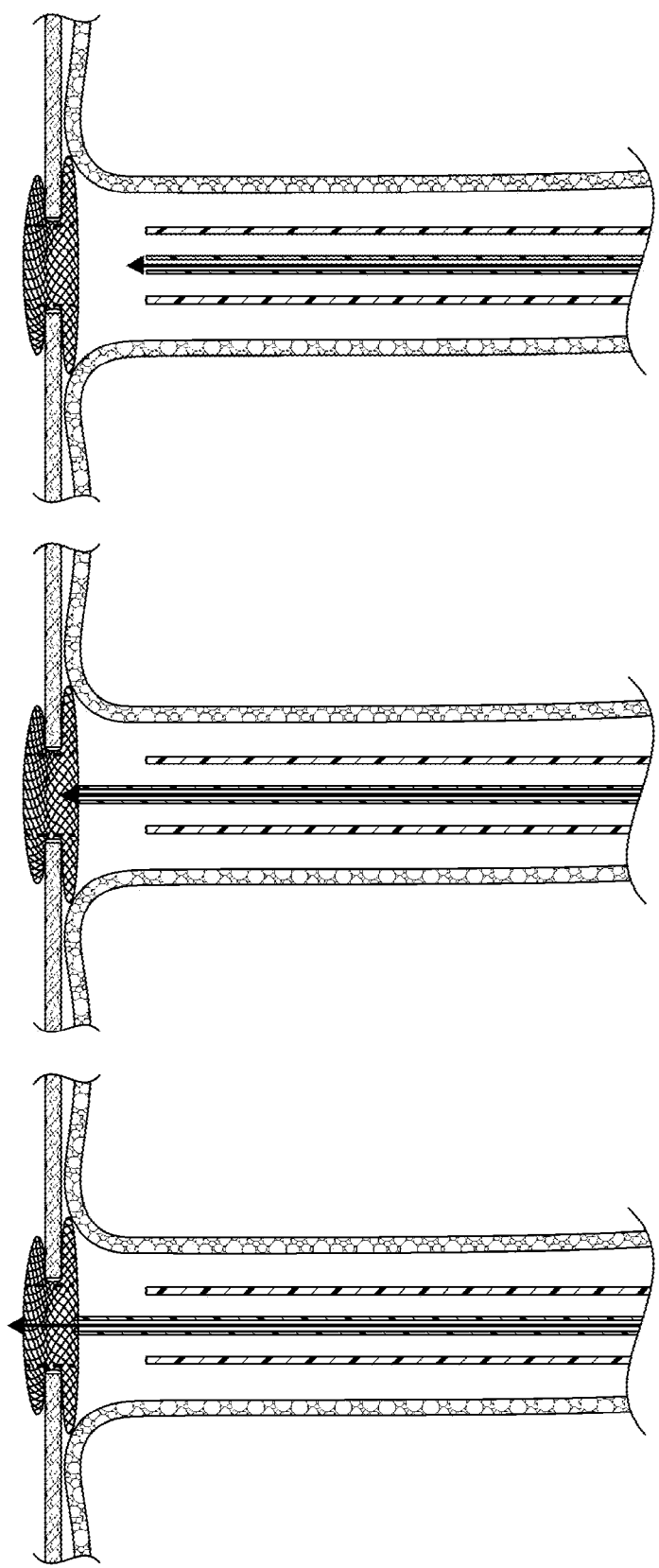

IN-SITU FENESTRATION DEVICES WITH ULTRASONIC CUTTER

CROSS-REFERENCE TO RELATED APPLICATION

This application claims the benefit of U.S. provisional application Ser. No. 63/406,553, filed Sep. 14, 2022, the disclosure of which is hereby incorporated in its entirety by reference.

TECHNICAL FIELD

The present disclosure relates to in-situ fenestration devices with an ultrasonic cutter.

SUMMARY

In one embodiment, an in-situ fenestration device is disclosed. The device includes a sheath, a sonic catheter extending with the sheath and having a cutting tool at a distal section thereof, and a balloon catheter extending within the sonic catheter. The cutting tool of the sonic catheter is configured to cut a fenestration in a graft material at a fenestration site of a stent graft upon being energized with ultrasonic energy at a cutting frequency.

In another embodiment, an in-situ fenestration device is disclosed. The device includes a sheath, a sonic catheter extending with the sheath and having a cutting tool at a distal section thereof, a balloon catheter extending within the sonic catheter, and a locating device carried on a distal end of a guidewire and configured to locate the fenestration site. The cutting tool of the sonic catheter is configured to cut a fenestration in a graft material at the fenestration site of a stent graft upon being energized with ultrasonic energy at a cutting frequency.

In yet another embodiment, a method of forming a fenestration in a graft material at a fenestration site of a stent graft is disclosed. The method includes delivering a balloon of a balloon catheter to the fenestration site. The method further includes locating a sonic cutting tool on a distal end of a sonic catheter at the fenestration site by inflating the balloon. The method also includes energizing the sonic cutting tool with ultrasonic energy at a cutting frequency to cut the fenestration in the graft material at the fenestration site of the stent graft.

BRIEF DESCRIPTION OF THE DRAWINGS

FIGS. 5A, 5B, and 5C depict schematic side views of various sonic cutting tools according to various embodiments.

FIGS. 7A through 7J depict partially cut away, schematic, side views of an in-situ fenestration procedure with a sonic cutter initial positioning feature.

FIGS. 7K through 7M depict partially cut away, schematic, side views of an in-situ fenestration procedure for a delivery grommet with a delivery device.

FIG. 9A depicts an isolated, schematic, perspective view of a self-expanding umbrella including a radio frequency (RF) electrode along a peripheral edge of the self-expanding umbrella.

FIG. 9B depicts a schematic, side view of first and second self-expanding umbrellas having first and second RF electrodes, respectively, aligned with each other where the first and second self-expanding umbrellas are tracked on a guidewire.

FIG. 9C depicts first and second self-expanding umbrellas misaligned along the guidewire.

FIGS. 16A through 16H depict the procedural steps of an in-situ fenestration device forming a fenestration in the graft material of a stent graft according to one embodiment.

FIG. 17A depicts a schematic, side view of a backboard in a deployed, unconstrained position.

FIG. 17B depicts an isolated view of a center portion of the backboard shown in FIG. 17A.

FIG. 17C depicts a schematic, side view of the backboard in an inverted position for removing the in-situ fenestration device from a patient's vasculature.

FIGS. 19A through 19E depict partially cut away, schematic side views of procedural steps for deploying a button into a fenestration in graft material.

FIGS. 23A, 23B, and 23C depict schematic views of an in-situ fenestration device in accordance with an embodiment where a backboard retrieves cut material when retracted.

FIGS. 25A through 25G depict schematic views of a procedure for deploying the button shown in FIGS. 24A, 24B, and 24C.

DETAILED DESCRIPTION

Figure 1A:
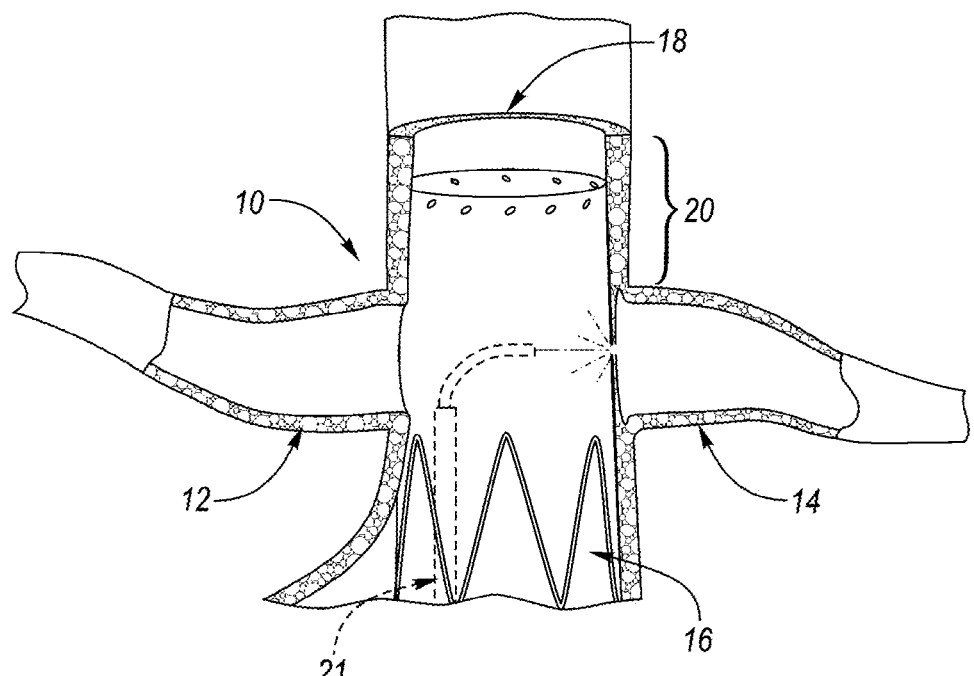
FIG. 1A depicts a partial cut away, schematic, side view of an abdominal aorta and right and left renal arteries extending therefrom where a stent graft excludes the right and left renal arteries from blood perfusion.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid, and renal arteries, the invention may also be used in any other body passageways (e.g., aortic valves, heart ventricles, and heart walls) where it is deemed useful.

In-situ fenestration (ISF) has seen limited applicability to aortic stent grafts for endovascular aneurysm repair (EVAR) and thoracic endovascular aneurysm repair (TEVAR). In-situ fenestration of aortic stent grafts can be used to maintain perfusion to blood vessels (e.g., aortic side branch arteries or peripheral arteries) located in an area excluded by a stent graft. In-situ fenestration may be used to fenestrate (e.g., create a new opening or hole) in a stent graft in-situ (e.g., in the place of the stent graft) following deployment of the stent graft within a vascular system. Application of ISF has been typically limited to removing unintentional coverage of blood vessels (e.g., arteries) upon deployment of a stent graft, but has rarely been used in elective scenarios.

FIG. 1A depicts a partially cut away, schematic, side view of abdominal aorta 10 and right renal artery 12 and left renal artery 14 extending from abdominal aorta 10. Right and left renal arteries 12 and 14 may be referred to generally as the renal arteries. Stent graft 16 includes proximal end 18 and a distal end (not shown). Proximal end 18 of stent graft 16 lands in landing zone 20 of abdominal aorta 10. Stent graft 16 extends from landing zone 20 to exclude perfusion to right renal artery 12 and left renal artery 14. An in-situ fenestration at the exclusion areas (e.g., using laser fenestration device 21) can be used to perfuse right renal artery 12 and left renal artery 14. Perfusion may result from blood flow through the fenestration alone or through a branch stent graft inserted into the fenestration after it is created and extending into the branch artery.

Figure 1B:
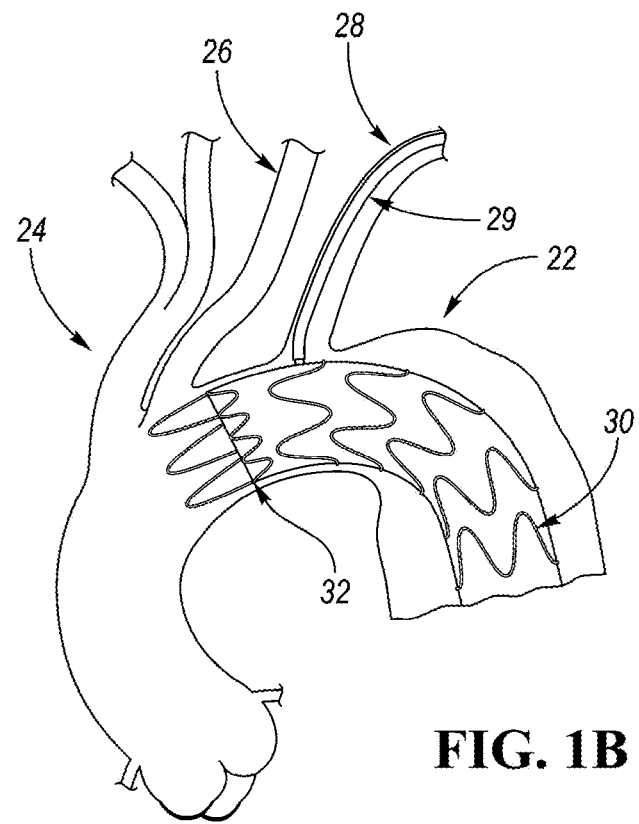
FIG. 1B depicts a partial cut away, schematic, side view of an aortic arch branching into a brachiocephalic artery, a left common carotid artery, and a left subclavian artery where a stent graft excludes the left subclavian artery from blood perfusion.

FIG. 1B depicts a partial cut away, schematic, side view of aortic arch 22 branching into brachiocephalic artery 24, left common carotid artery 26, and left subclavian artery 28. Brachiocephalic artery 24, left common carotid artery 26, and left subclavian artery 28 may be referred to generally as side branch arteries. Stent graft 30 includes proximal end 32 and a distal end (not shown). Stent graft 30 extends to exclude perfusion to left subclavian artery 28. An in-situ fenestration (e.g., using laser fenestration device 29) at the exclusion area created at left subclavian artery 28 can be used to perfuse left subclavian artery 28 (e.g., via the fenestration or a later-deployed branch stent graft).

In-situ fenestration may provide a solution for implementing stent grafts with patients having hostile neck anatomy within their abdominal aorta. Current stent graft seal technology is unsuitable for many aortic anatomies. Many aortic abdominal and thoracic aortic aneurysms present either a relatively short seal zone (e.g., 0 to 10 millimeters) and/or a high degree of landing zone angulation. Examples of such anatomies include a short neck aneurysm, no neck thoracoabdominal aneurysm, reverse conical neck, and highly angled aneurysm neck with a short landing zone inner curve. Under these circumstances, an alternative landing zone may be used that excludes perfusion to peripheral arteries (e.g., the renal arteries). In-situ fenestration may be used to open these excluded areas to permit blood perfusion. However, adequate in-situ fenestration processes and related devices/systems have not been proposed to realize the potential of in-situ fenestration in this regard.

Accordingly, clinicians (e.g., doctors or physicians) have investigated other techniques for modifying stent grafts for EVAR and TEVAR patients. The existing techniques (e.g., dedicated off-the-shelf multibranch devices, custom-made multibranch devices, clinician modified devices, and peripheral techniques) do not adequately modify stents grafts to completely address blood perfusion.)

For instance, dedicated off-the-shelf multibranch devices may have low patient applicability due to variability in the anatomy of patients. The geometry to accommodate multiple branches on a dedicated branch device can be complicated to determine. Procedures to deploy these devices are complex. Branching canulation and/or stenting can be complicated because the devices are susceptible to rotational or axial misalignment.

An alternative technology is a custom-made multibranch device. However, these devices require a significant lead time (e.g., 6 to 8 weeks) and are not available for emergent cases. Moreover, custom ordered devices may still be susceptible to axial and rotational misalignment.

Clinicians have modified stent grafts themselves before deploying the stent graft in the vascular system of the patient. Physicians can partially deploy an off-the-shelf stent graft on a sterile field and make fenestrations based on patient specific anatomy. This type of "back table" modification of an off-the-shelf stent graft may have one or more benefits. Eye cautery (e.g., thermal energy) may be used to clean and/or seal any frayed and/or cut fiber ends at the fenestration boundary. The size of the fenestration is customizable without post dilation, which may cause material damage. The fenestrations can be made using three-dimensional (3D) reconstructions from patient specific computed tomography (CT) scans. The fenestrations can be reinforced with sutures and/or guidewires to make a durable interface between the main stent graft and the branch stent graft. However, these procedures include unloading of the stent graft so that it can be modified with a fenestration. Reloading the stent graft is a challenge due to the low profile and high packing density of the stent graft in the radially compressed, delivery state. These modifications are typically labor and time intensive.

Techniques for providing blood flow to peripheral blood vessels used in connection with off-the-shelf stent grafts have also been proposed. Clinicians can deploy off-the shelf stent grafts in parallel with these techniques to permit blood perfusion to peripheral arteries and respective organs. Examples of these types of technologies chimneys, snorkels, and sandwich techniques. A chimney structure may be applied in the abdominal aorta and may include a renal chimney and a seal zone distal to a lower chimney. A different structure may be applied in the aortic arch where blood flows into a chimney from the aortic arch and blood flows out of the chimney into the left common carotid artery, and blood flows into a periscope from the aortic arch and blood flows out of the periscope into the left subclavian artery. Another technique is referred to as a sandwich. Blood flows into the celiac artery and superior mesenteric artery (SMA) from sandwich parallel chimneys. These techniques may have one or more of the following benefits: (1) available for emergent cases; (2) configurations can be adapted for patient-specific anatomies (e.g., ballerina techniques); and/or (3) planning using 3D reconstructions from patient specific CT scans. However, these techniques have durability concerns and potential mid or long-term occlusion risks relating to challenging hemodynamics.

Due to one or more drawbacks of the existing technologies identified above, there has been interest in developing in-situ fenestration technology that addresses one or more of the drawbacks identified above. In-situ fenestration encompasses processes in which apertures are made in a fully or partially deployed stent graft inside of a patient. Under limited circumstances, in-situ fenestration has been employed to provide perfusion in the aortic arch, the visceral segment, and the iliac arteries. In the aortic arch, in-situ fenestration can be made in a retrograde direction (e.g., outside of the stent graft) using supra-aortic access. Other anatomies may use in situ fenestration using an antegrade technique (e.g., inside the stent graft). In-situ fenestration may have one or more of the following benefits: (1) provides a multibranch solution independent of patient anatomical constraints thus providing for a larger applicability; (2) can be performed using off-the-shelf stent grafts; and/or (3) may avoid time-consuming "back-table" modification and technically challenging reloading into delivery systems.

However, current in-situ fenestration techniques suffer from one or more drawbacks. Current in-situ fenestration methods result in relatively small size apertures where aggressive post-dilation is used to accommodate a branch stent graft. Needle in-situ fenestration uses a needle to create an initial fenestration. Laser fenestration uses a laser ablation catheter having a diameter of 2.0 to 2.5 millimeters. Radio frequency (RF) ablation may also be used. One example of an RF ablation method uses a 0.035 inch powered wire. As a drawback, damage to the graft material during fenestration expansion adds to procedural variability and makes durability testing difficult. Additionally, lack of standardized protocols results in lack of consistency in fenestrations, thereby inhibiting consistent anticipation of intermediate and long-term durability.

In one or more embodiments, in-situ fenestration process and/or related devices are disclosed that at least partially addresses one or more of the following drawbacks and/or at least partially provides one or more of the following benefits. A potential drawback of existing technology is anatomical variability limiting patient applicability of dedicated off-the shelf branch devices. A potential benefit of in-situ fenestration is customization of off the shelf stent grafts that is independent of anatomical constraints. Custom devices have been proposed but take a relatively long time (e.g., 6-8 weeks) for manufacture and deliver, and may not be available for emergent cases. A potential benefit of in-situ fenestration is application to off-the-shelf devices with no manufacturing or shipping delays.

Another potential drawback relates to "back table" modification of off-the-shelf devices by clinicians. These modified devices are difficult to reload, limiting adoption of this method. In-situ modification of a stent graft occurs in-situ, and thereby eliminating the step of reloading the device into a delivery system. Custom and "back table" modified devices are susceptible to axial or rotational misalignment which can impact vessel canulation. Fenestrations created in-situ after the deployment of a stent graft are independent of the position of the main graft.

Current in-situ fenestration procedure lack standardization in terms of initial fenestration source and post dilation procedures. A potential benefit of standardization would be the reduction or elimination of severe post dilation steps that can cause unpredictable damage to a graft material.

Current in-situ fenestration procedures may result in cut fibers and/or ripped material. These drawbacks may represent a source of procedural variability and may limit the long-term durability and seal of the fenestration and branch stent graft interface. One or more embodiments disclose a method for sealing cut fibers that help prevent continued breakdown of the fenestration and branch stent graft interface.

Current fenestration techniques start with a small initial fenestration that is aggressively post dilated to accommodate a branch graft which can result in the tearing of the graft material. Some graft materials use cutting balloons for post dilation, which may cause additional cut fibers and material damage. One or more embodiments disclose a method and/or device for forming a fenestration in-situ of a size and shape that involves little or no post dilation and/or cutting balloons.

Power sources (e.g., laser and RF ablation) for current in-situ fenestrations may create steam bubbles and generate char particles that can pose embolic risk. One or more embodiments disclose a method and/or device to allow in-situ fenestration creation while minimizing steam bubbles and char formation.

In one or more embodiments, an in-situ fenestration device with an ultrasonic cutter is disclosed. The in-situ fenestration device may include a sonic catheter and a balloon catheter. The sonic catheter may include a sonic cutting tool configured to cut a fenestration upon being energized with ultrasonic energy. The balloon catheter may be configured to capture the fenestration and/or locate a branch vessel.

Figure 2A:
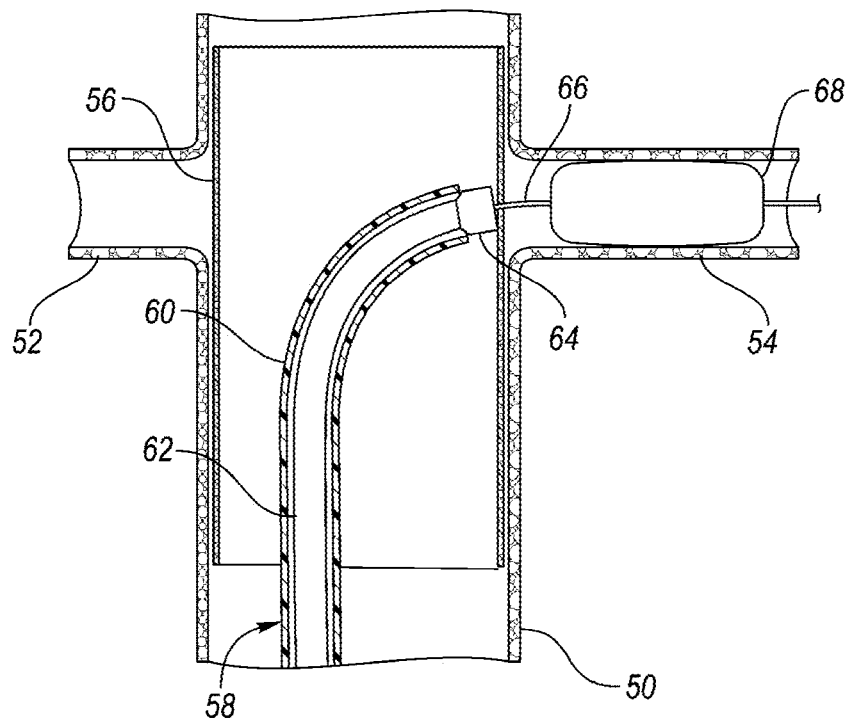
FIG. 2A depicts a partially cut away, schematic, side view of an abdominal aorta and right renal artery and a left renal artery with an ultrasonic in-situ fenestration system extending therein.

FIG. 2A depicts a partially cut away, schematic, side view of abdominal aorta 50 and right renal artery 52 and left renal artery 54 extending from abdominal aorta 50. Stent graft 56 is deployed in a radially expanded position within abdominal aorta 50. Ultrasonic in-situ fenestration system 58 extends within stent graft 56. Ultrasonic in-situ fenestration system 58 includes steerable sheath 60, sonic catheter 62 configured to track within steerable sheath 60, and sonic cutting tool 64 disposed on a distal end of sonic catheter 62. Steerable sheath 60 and sonic catheter 62 are both configured to track over guidewire 66. Balloon catheter 68, shown in left renal artery 54, is also configured to track over guidewire 66. While FIG. 2A depicts application of the ultrasonic in-situ fenestration system to the renal arteries, in other embodiments, the ultrasonic in-situ fenestration system may be applied to other branch arteries (e.g., celiac, SMA, BCA, LCC, LSA, etc.).

Figure 2B:
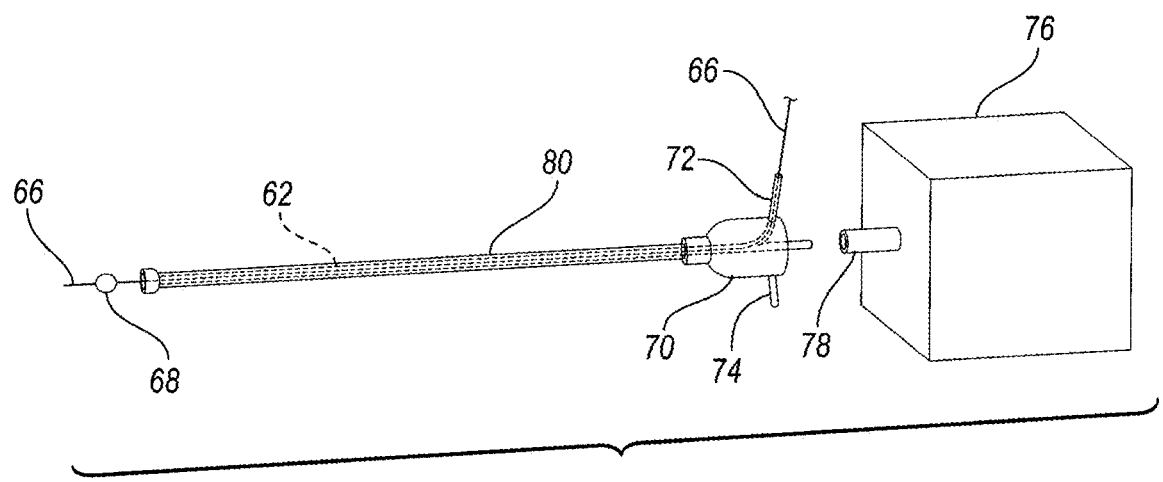
FIG. 2B depicts a schematic, perspective view of an ultrasonic in-situ fenestration system.

FIG. 2B depicts a schematic, perspective view of ultrasonic in-situ fenestration system 58. In addition to FIG. 2B depicting sonic catheter 62, guidewire 66, and balloon catheter 68, FIG. 2B also depicts catheter hub 70 including guidewire port 72 configured to track guidewire 66 and flushing port 74 configured to allow a saline flush through steerable sheath 60. Sonic generator 76 is configured to connect to sonic catheter 62 through converter 78 configured to deliver ultrasonic energy to sonic cutting tool 64 through sonic catheter 62. As shown in FIG. 2B, ultrasonic in-situ fenestration system 58 includes integrated outer sheath 80 configured to cover sonic cutting tool 64.

In one or more embodiments, ultrasonic energy is transferred along sonic catheter 62 to create oscillation (e.g., longitudinal) of sonic cutting tool 64 to cut through the graft material of stent graft 56 at a fenestration site, thereby providing access to left renal artery 54 through the graft material. The ultrasonic energy may have a frequency in a range to cut through the types of fabrics used for the graft material. The frequency may be any of the following or in a range of any two of the following: 20, 21, 22, 23, 24, 25, 26, 27, 28, 29, 30, 31, 32, 33, 34, 35, 36, 37, 38, 39, and 40 kHz. Using ultrasonic energy for the cutting operation may minimize or eliminate fraying and/or burning of the graft material. The ultrasonic energy may also simultaneously cut/punch an in-situ fenestration and seal the edges thereof (e.g., the edges of a polymeric fabric).

Figure 3:
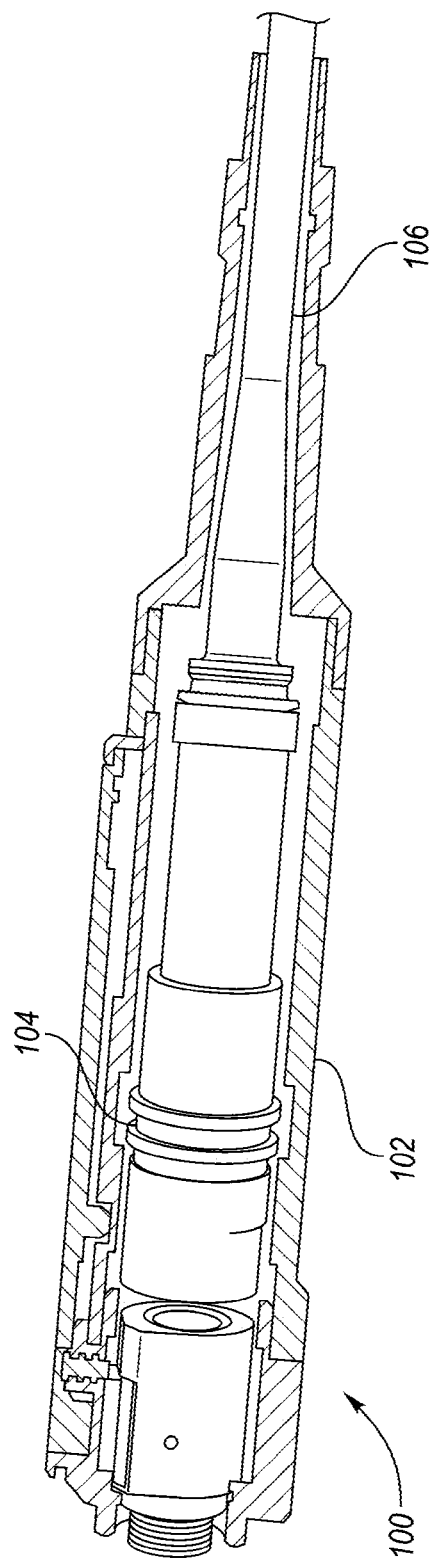
FIG. 3 depicts a partially cut away, schematic, side view of a transducer according to one embodiment.

In one or more embodiments, a transducer may be placed outside of the body (e.g., the patient's vasculature). The transducer may be configured to transmit mechanical energy through a full length of a sonic catheter to a distal end thereof. FIG. 3 depicts a partially cut away, schematic side view of transducer 100. Transducer 100 includes encapsulation cover 102 encapsulating piezoceramic ring 104 connected to tip connecting device 106 connected to a proximal end of a sonic catheter. Tip connecting device 106 may be formed of a titanium wire.

Alternatively or in addition, a transducer (e.g., a miniaturized transducer) may be placed in a middle portion of a sonic catheter to reduce the distance of mechanical transmission. The miniaturized transducer may be a piezo ceramic transducer with a miniaturized converter. The transducer may be hollow to allow passage of a guidewire and other devices (e.g., a balloon catheter). Non-limiting examples of piezo-ceramic transducers include multilayer chips, plates, mini spheres, miniature benders, disks, mini rings, miniature tubes, and hexagonal plates.

Sonic catheter 62 may be a hollow hypotube or cable. In one or more embodiments, the hollow cable may be the Helical Hollow Strand® product available from Fort Wayne Metals Research Products, LLC. Sonic catheter 62 may be made from a Nitinol material or a titanium material. In one or more embodiments, sonic catheter 62 is configured to provide energy transfer from an ultrasonic generator (e.g., generator 76) to a distal end of sonic catheter 62 where a cutting tool (e.g., sonic cutting tool 64) is located. Sonic catheter 62 may have a lumen extending the center thereof. The lumen may track over a guidewire (e.g., a 0.035 inch guidewire) and be configured to allow a balloon catheter (e.g., balloon catheter 68) to pass through.

An integrated outer sheath (e.g., integrated outer sheath 80) is configured to cover the cutting tool (e.g., sonic cutting tool 64). The integrated outer sheath may be configured to allow the sonic catheter (e.g., sonic catheter 62) with the sonic cutting tool (e.g., sonic cutting tool 64) to advance through a separate steerable sheath (e.g., steerable sheath 60) without the cutting tool skiving or getting caught on the inside of the steerable sheath. Once the cutting tool is near the inside of the graft material, the integrated outer sheath may be retracted proximally (e.g., 1 to 2 centimeters) to expose the cutting tool for performing the cutting operation.

In one or more embodiments, a solution (e.g., a saline solution) may be pumped through either the lumen of the sonic catheter or between the outer diameter of the cutting tool and the inner diameter of the integrated sheath to reduce friction between the vibrating sonic catheter and to minimize or prevent excessive heat generation.

Figure 4:
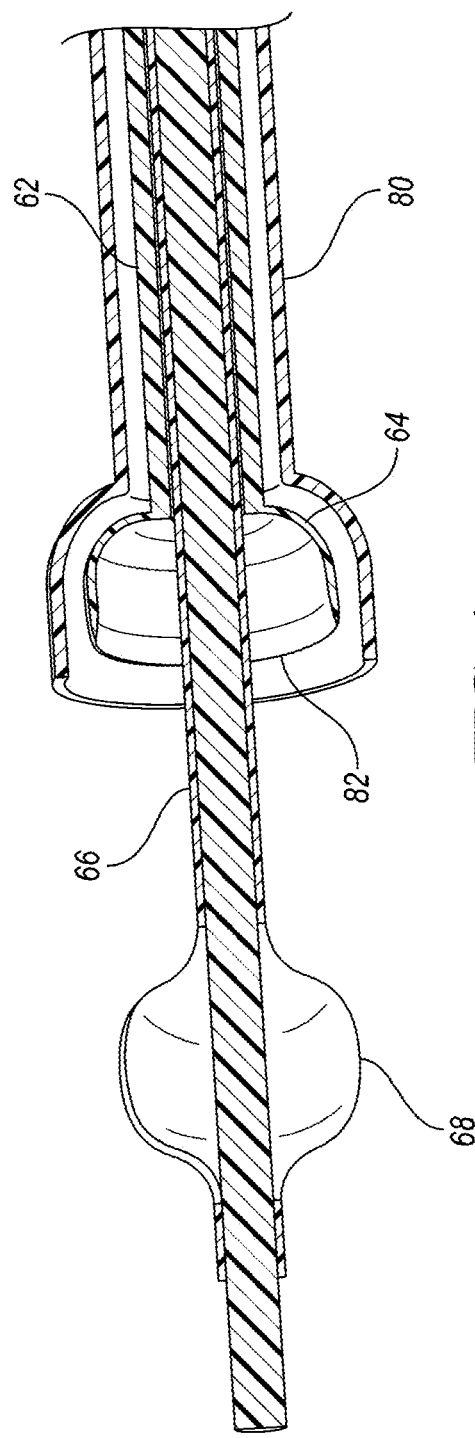
FIG. 4 depicts a partially cut away, schematic, side view of an ultrasonic in-situ fenestration system including a balloon catheter, a sonic cutting tool, and an integrated outer sheath.

FIG. 4 depicts a partially cut away, schematic, side view of ultrasonic in-situ fenestration system 58 including balloon catheter 68, sonic cutting tool 64 and integrated outer sheath 80. As shown in FIG. 4, balloon catheter 68 is co-axial with sonic cutting tool 64 and is configured to secure cut graft material at the in-situ fenestration site. Sonic cutting tool 64 is configured to cut by longitudinal ultrasonic vibration. Integrated outer sheath 80 is configured to protect sonic cutting tool 64 and to infuse a solution (e.g., a saline solution) to reduce friction between a vibrating sonic catheter and to minimize or prevent heat generation. As shown in FIG. 4, sonic cutting tool 64 is disposed at the distal end of sonic catheter 62. Sonic cutting tool 64 includes a sharp edge 82 configured to facilitate cutting through a graft material as sonic cutting tool 64 vibrates longitudinally through ultrasonic energy vibrations transmitted down the shaft of sonic catheter 62.

The sharp edge of sonic cutting tool may be formed of a titanium alloy material or a special alloy blade with 62 on the Rockwell scale. FIGS. 5A, 5B, and 5C depict schematic side views of various sonic cutting tools according to various embodiments. Cutting tool 150 shown in FIG. 5A includes proximal end 152 and distal end 154. Cutting tool 150 tapers outward from proximal end 152 to distal end 154 to form a conical shape. Distal end 154 includes triangular cutting elements with cutting edge 156 to form an overall circular saw tool profile. Cutting tool 160 shown in FIG. 5B includes proximal end 162 and distal end 164. Cutting tool 160 tapers outward from proximal end 162 to distal end 164 to form a conical shape. Distal end 164 includes cutting edge 166 including a continuous cutting element forming an overall circular profile. Cutting tool 170 shown in FIG. 5C includes proximal end 172 and distal end 174. Cutting tool 170 tapers outward from proximal end 172 into a constant diameter region extending to distal end 174. Distal end 174 includes cutting edge 176 including a continuous cutting element forming an overall circular profile.

Figures 5D, 5E, 5F:
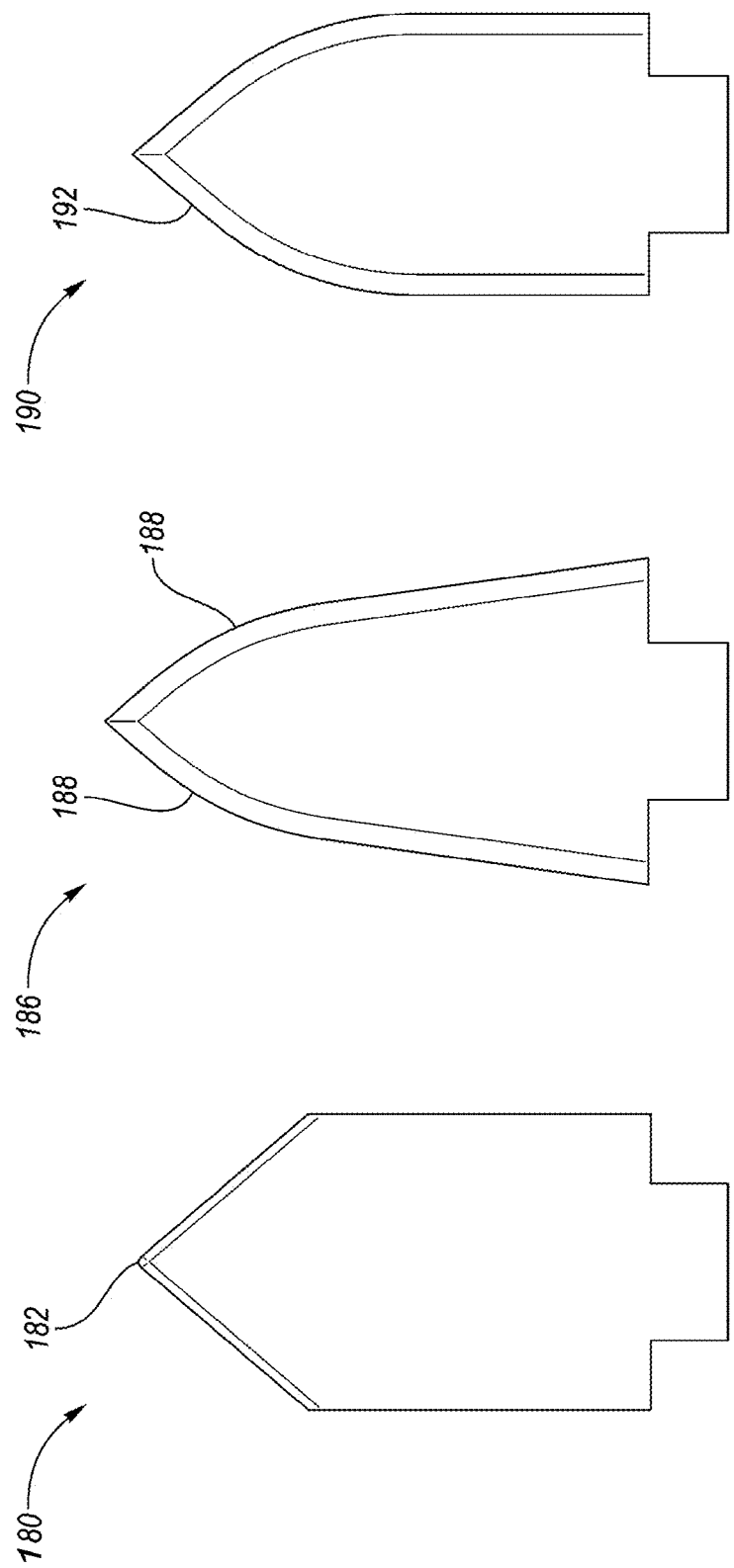
FIG. 5D is an isolated, schematic side view of a cutting element with a barb.
FIG. 5E is an isolated, schematic side view of a cutting element with chamfers.
FIG. 5F is an isolated, schematic side view of a cutting element with chamfers.

The cutting elements may have barb(s) configured to increase contact area with the graft material and/or chamfer(s) to increase sharpness. For instance, cutting edge 156 may be carried on the barb(s). FIG. 5D is an isolated, schematic side view of cutting element 180 with barb 182. FIG. 5E is an isolated, schematic side view of cutting element 186 with chamfers 188. FIG. 5F is an isolated, schematic side view of cutting element 190 with chamfers 192.

In an alternative embodiment, one or more micro transducers are disposed about the circumference of the cutting edge of the cutting tool at the distal end thereof. The one or more micro transducers are configured to drive the cutting elements on the cutting edge. Each of the micro transducers may be configured to independently drive a specific cutting element. The cutting elements may be micro cutters or micro needles configured to vibrate upon actuation of the micro transducers to vibrate and to cut a fenestration in the graft material. The use of individual micro cutters may enable a collapsible type of cutting head with a reduced profile.

Figure 6A:
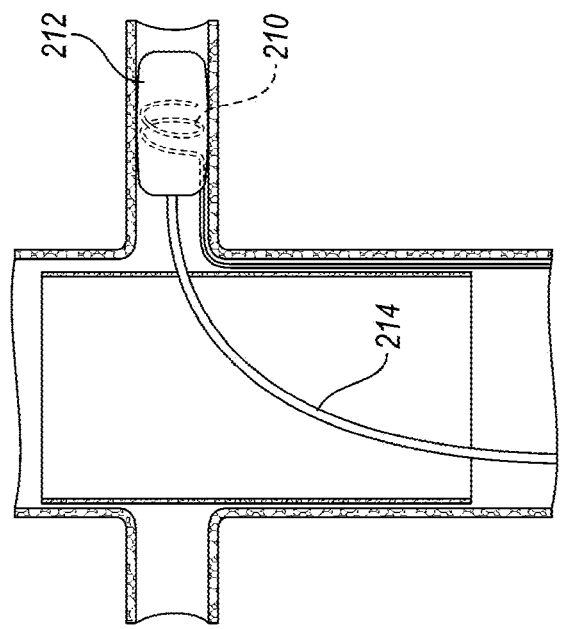
FIG. 6A depicts a partially cut away, schematic side view of a locating device delivered on the distal end of a guidewire situated between a stent graft and the wall of an abdominal aorta.
Figure 6B:
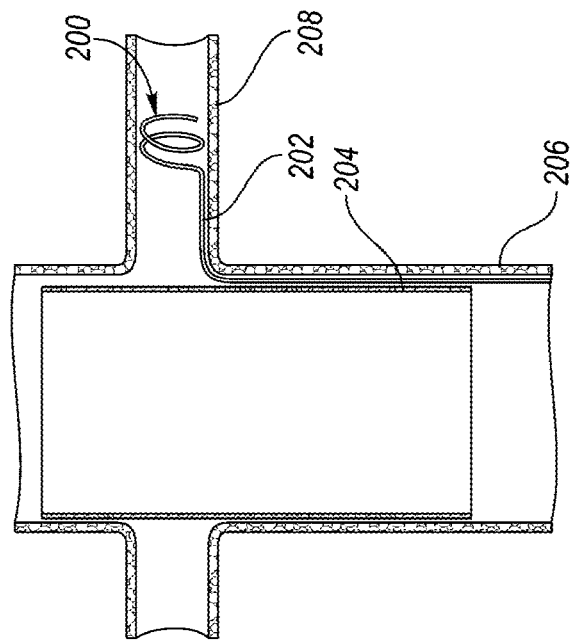
FIG. 6B depicts a partially cut away, schematic side view of the locating device situated within a balloon at the distal end of a catheter.
Figure 6D:
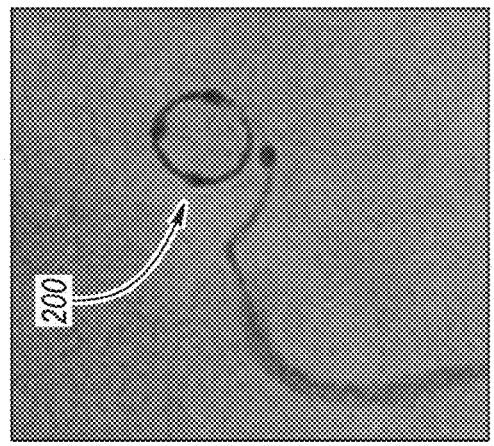
FIG. 6D is a second fluoro imaging view depicting the locating device with the spiral profile.
Figure 6C:
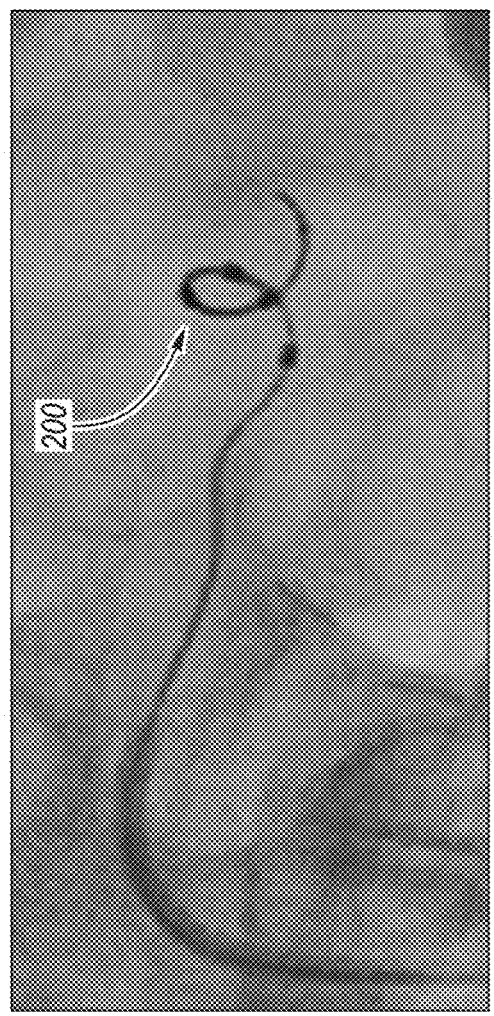
FIG. 6C is a first fluoro imaging view depicting the locating device with the spiral profile.

The in-situ fenestration system of one or more embodiments may have a component to identify where to create a fenestration within the graft material of a stent graft. FIG. 6A depicts a partially cut away, schematic side view of locating device 200 delivered on the distal end of guidewire 202 situated between stent graft 204 and the wall of abdominal aorta 206. As shown in FIG. 6A, locating device 200 is placed within renal artery 208 extending from abdominal aorta 206. Locating device 200 has a spiral profile readily apparent on a fluoro imaging view. FIG. 6C is a first fluoro imaging view depicting locating device 200 with the spiral profile. FIG. 6D is a second fluoro imaging view depicting locating device 200 with the spiral profile. FIGS. 6C and 6D depict an example of how a renal artery ostium may be using AP (first fluoro imaging view) and "down the barrel" (second fluoro imaging view) views. FIG. 6B depicts a partially cut away, schematic side view of locating device 210 situated within balloon 212 at the distal end of catheter 214. Locating device 210 may be expanded by balloon 212 so that it is a renal ostium beacon on fluoro imaging views.

An initial fenestration may be made into the graft material of a stent graft to gain access to a renal artery. The diameter of the initial fenestration may be any of the following diameters or in a range of any two of the following diameters: 0.030, 0.035, 0.040, 0.045, and 0.050 inches.

In one or more embodiments, a mechanical puncture may be used to make the initial fenestration. A guide wire or needle (e.g., a Brockenbrough needle available from Medtronic PLC of Minneapolis, Minnesota) may be placed through a steerable catheter (e.g., Mullins sheath available from Medtronic PLC of Minneapolis, Minnesota) oriented towards graft material facing a renal ostium. The needle or the stiff proximal end of the guidewire may be pushed forward to puncture the graft material. An exchange catheter may be placed over the guidewire and into the renal ostium and the guidewire may then be removed. The guidewire may be reversed within the exchange catheter so that the soft, atraumatic end of the guidewire is in the renal ostium.

Alternatively, an energy-based fenestration device may be used to make the initial fenestration. A power guidewire (e.g., a 0.035 inch PowerWire® RF guidewire available from Baylis Medical Company Inc. of Mississauga, Ontario, Canada) to burn a relatively small hole through the graft material. Once the relatively small hole is formed, a guidewire may be placed through the hole into the renal ostium. In another embodiment, a laser probe is configured to burn a hole through the graft material and to place a 0.014 inch guidewire through the initial fenestration into the renal ostium.

FIGS. 7A through 7J depict partially cut away, schematic, side views of an in-situ fenestration procedure with a sonic cutter initial positioning feature. In FIG. 7A, transfemoral arterial access is gained and guidewire 250 is tracked in-situ into stent graft 252 of abdominal artery 254. The graft material adjacent renal branch artery 256 is punctured using any of the initial fenestration operations identified above. As shown in FIG. 7B, steerable guide sheath 258 and dilator 260 are tracked over guidewire 250 until dilator 260 contacts the inner surface of the graft material adjacent renal branch artery 256. As shown in FIG. 7C, catheter 262 having sonic cutter 264 and inline capture balloon 266 are tracked over guidewire 250 and through steerable guide sheath 258 up to the inner surface of stent graft 252. Steerable guide sheath 258 is configured to protect the patient's vasculature from sonic cutter 264, which may be rigid. As shown in FIG. 7D, inline capture balloon 266 is advanced along guidewire 250 through the initial fenestration at the puncture site so that it is in renal branch artery 256. As shown in FIG. 7E, inline capture balloon 266 is inflated to an equivalent diameter of renal branch artery 256 (e.g., about 4 mm) to centralize guidewire 250 in renal branch artery 256, thereby centralizing catheter 262 for the ultrasonic vibration operation. Contrast may be used within inline capture balloon 266 to verify placement within renal branch artery 256.

As shown in FIG. 7F, sonic cutter 264 is advanced out of steerable guide sheath 258 until resistance is sensed as cutter edge 268 contacts the inner surface of the graft material. Alignment of sonic cutter 264 and renal branch artery 256 for the desired in-situ fenestration site may be confirmed using a fluoro image in the plane of the ostium of renal branch artery 256. Alternatively, the plane of the ostium may be identified from a pre-procedural computed tomography (CT) scan. As depicted in FIG. 7G, an ultrasonic energy source is activated to vibrate sonic cutter 264 to cut the graft material. Fluoro imaging may be used to confirm that the cut is successfully completed, by confirming as shown in FIG. 7G, cutter edge 268 is external to the stent frame of stent graft 252 after this operation is completed. As shown in FIG. 7H, sonic cutter 264 is retracted slightly back into stent graft 252. Cut graft remnant 270 is captured between inline capture balloon 266 and sonic cutter 264 and the central puncture of cut graft remnant 270 is suspended on guidewire 250. As shown in FIG. 7I, inline capture balloon 266 is partially deflated to a diameter relatively smaller than the diameter of renal branch artery 256 (e.g., slightly less than 4 mm). At this point in the in-situ fenestration procedure, blood flow is restored to renal branch artery 256, thereby stopping the occlusion short of any potential time limit for an occlusion. As shown in FIG. 7J, inline capture balloon 266 is retracted through the fenestration, thereby capturing cut graft remnant 270. Inline capture balloon 266 is then pulled into the open cavity of sonic cutter 264 and into steerable guide sheath 258. Catheter 262 and steerable guide sheath 258 are subsequently removed, while guidewire 250 may be left in place for placement of a branch stent graft or covered stent.

Figure 8A:
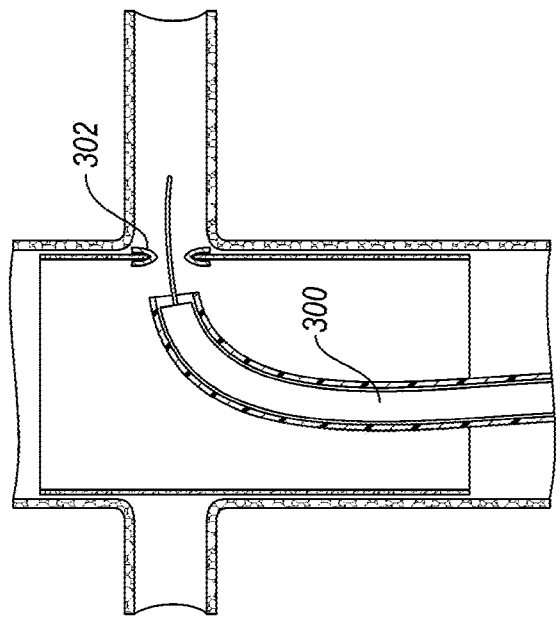
FIG. 8A depicts a partially cut away, schematic, side of a delivery device configured to deliver the grommet to a fenestration.
Figure 8B:
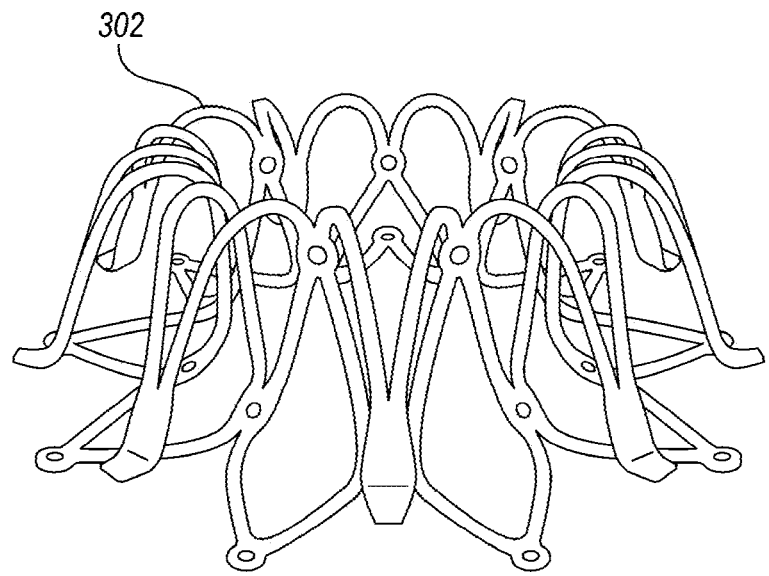
FIG. 8B depicts a side, elevational view of the grommet shown in FIG. 8A.
Figure 8C:
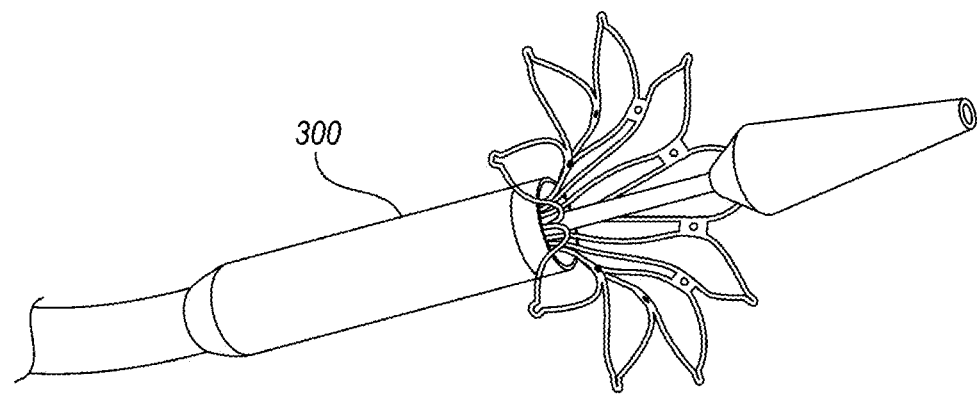
FIG. 8C depicts a perspective view of the delivery device including the grommet.

In one or more embodiments, a grommet may be utilized to enlarge the diameter of and/or reinforce the fenestration. In one or more embodiments, the grommet may enlarge the fenestration from about 6 mm to about 8 mm. The grommet may be configured to confine frayed edges and provide a smooth transition for a branch stent graft or covered stent. The grommet may be made from a self-expanding material such as a Nitinol material. The grommet may be configured such that a balloon expandable graft may also be expanded to make the opening larger. FIG. 8A depicts a partially cut away, schematic, side view of delivery device 300 configured to deliver grommet 302 to a fenestration. FIG. 8B depicts a side, elevational view of grommet 302. FIG. 8C depicts a perspective view of delivery device 300 including grommet 302.

Figure 7M:
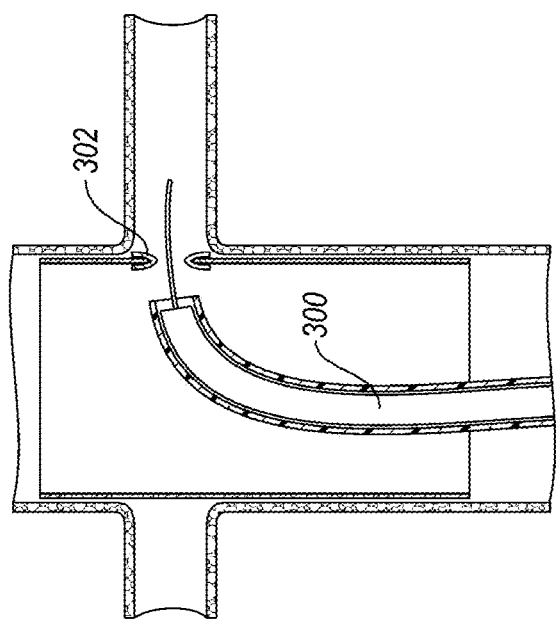

FIGS. 7K through 7M depict partially cut away, schematic, side views of an in-situ fenestration procedure for delivering grommet 302 with delivery device 300. As shown in FIG. 7K, delivery device 300 is inserted through steerable guide sheath 258 to the fenestrated portion of the graft material. As shown in FIG. 7L, distal arms 304 are deployed to go behind the graft material. The graft frame alignment can be imaged using fluoro to help the positioning of distal arms 304. As shown in FIG. 7M, grommet 302 is deployed and delivery device 300 is removed from the vasculature of the patient. Catheter 300 and steerable guide sheath 258 are subsequently removed, while guidewire 250 may be left in place for placement of a branch stent graft or covered stent.

One or more embodiments of the in-situ fenestration device with an ultrasonic cutter may have one or more of the following benefits. The ultrasonic cutting tip may use a relatively small amount of force against the stent graft material, thereby resulting in a safe, controlled cutting step. Accordingly, there may be a low risk in displacing the in-situ graft or causing trauma to a patient's vasculature. The ultrasonic cutting motion may reduce fraying of the cut graft material. The ultrasonic frequency may be selected/optimized to be atraumatic to the graft stent and the anatomy of the patient. The ultrasonic cutting device of one or more embodiments produces a predictable fenestration size and shape due to the circular fixed size cutting tip. The ultrasonic energized cutting tip of one or more embodiments is configured to cut through graft material in less than 10 seconds, thereby reducing procedural time and restoring blood flow to the renal branch artery. The inline capture balloon of one or more embodiments may prevent embolisms by preventing the removed fabric from breaking free. An optional, expandable grommet may provide a smooth and durable transition from the stent graft to a covered stent through the fenestration.

In one or more embodiments, an in-situ fenestration device with a pair of opposing congruent self-expanding members (e.g., an umbrella pair) is disclosed. In one or more embodiments, each member has a three-dimensional shape (e.g., a pyramidal shape, a conical shape, a hemispheric shape, an umbrella shape, etc.) The umbrella shape may be formed from a number of triangular shaped panels (e.g., eight (8) panels as shown in the Figures). The number of triangular panels may be any of the following values or in a range of any two of the following values: 3, 4, 5, 6, 7, 8, 9, 10, 11, and 12. The in-situ fenestration device is configured to create an in-situ fenestration in an arterial stent graft. The self-expanding umbrella pair may be loaded into a delivery system and may be enclosed within a capsule, thereby allowing the umbrella to be recaptured and redeployed so multiple fenestrations (e.g., 2 or more) may be made during the same procedure.

In one or more embodiments, the self-expanding umbrella pair includes a first umbrella configured to be deployed on the inside of the graft material of a stent graft and a second umbrella configured to be deployed on the outside of the graft material. The self-expanding umbrella pair may be brought together during the procedure to contain any byproducts produced within the umbrella, thereby mitigating embolism risk to the patient.

The self-expanding umbrella pair may efficiently and repeatably create an in-situ fenestration while ensuring the procedure is atraumatic to the patient's vasculature and the stent graft. The self-expanding umbrella pair may be configured to visually demonstrate alignment, remove the remnant graft material, and/or create multiple fenestrations without removing the delivery device from the patient.

FIG. 9A depicts an isolated, schematic, perspective view of self-expanding umbrella 350 including a radio frequency (RF) electrode along peripheral edge 352 of self-expanding umbrella 350. FIG. 9B depicts a schematic, side view of first and second self-expanding umbrellas 354 and 356 having first and second RF electrodes 358 and 360, respectively, aligned with each other where first and second self-expanding umbrellas 354 and 356 are tracked on guidewire 362. In the aligned state shown in FIG. 9B, RF energy is delivered through first and second RF electrodes 358 and 360 to cut the graft material at a fenestration site. FIG. 9C depicts first and second self-expanding umbrellas 354 and 356 misaligned along guidewire 362. In this misaligned state, first and second RF electrodes 358 and 360 are not energized, thereby no RF energy is being delivered.

The self-expanding umbrella pair may be packed in a relatively small delivery package to mitigate trauma to a patient's vasculature. In one or more embodiments, the self-expanding umbrellas are made of a fine, self-expanding mesh sewn into a high strength fabric. The peripheral edge of each self-expanding umbrella has an RF electrode configured to create a fenestration in a stent graft at a fenestration site. One of the umbrellas is configured to detect the other of the umbrellas such that RF energy is only applied when the peripheral edges of the umbrellas contact each other. Since RF energy is not applied until proper alignment is achieved, damage to the stent graft may be mitigated or prevented. Graft materials, steam bubbles, and other byproducts from the procedure are contained within the inner cavity of the umbrella pair to avoid or mitigate patient harm. In one or more embodiments, radiopaque (RO) markers disposed at the peripheral edge of each of the umbrellas assist in alignment of the in-situ fenestration device.

Figure 10:
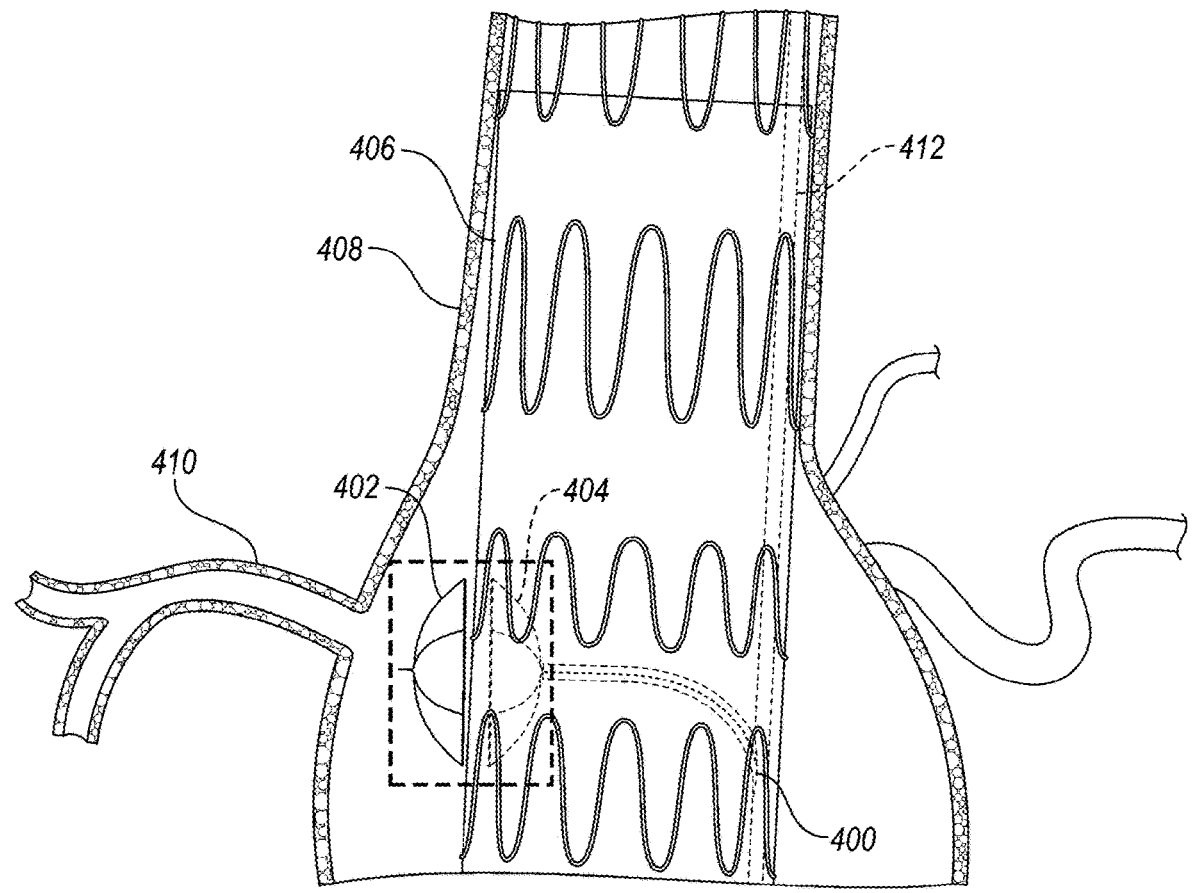
FIG. 10 depicts a partially cut away, schematic side view of an in-situ fenestration device with first and second self-expanding umbrellas in an expanded position on either side of a stent graft situated in an abdominal aorta.

FIG. 10 depicts a partially cut away, schematic side view of in-situ fenestration device 400 with first and second self-expanding umbrellas 402 and 404 in an expanded position on either side of stent graft 406 situated in abdominal aorta 408. In-situ fenestration device 400 is configured to make a fenestration at a fenestration site aligned with the ostium of renal artery 410. As shown in FIG. 10, in-situ fenestration device 400 is configured to track along guidewire 412.

Figure 11D:
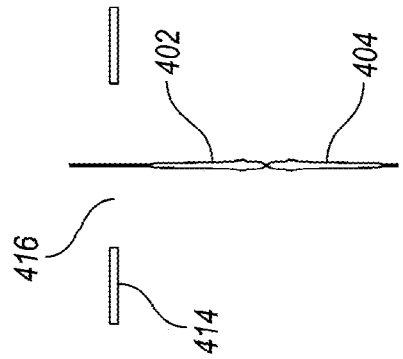
FIGS. 11A through 11D depict schematic, side views of an in-situ fenestration procedure using a self-expanding umbrella pair.
Figure 11C:
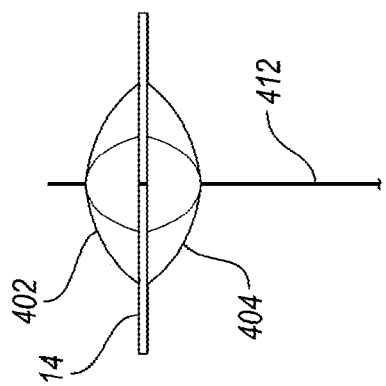
Figure 11B:
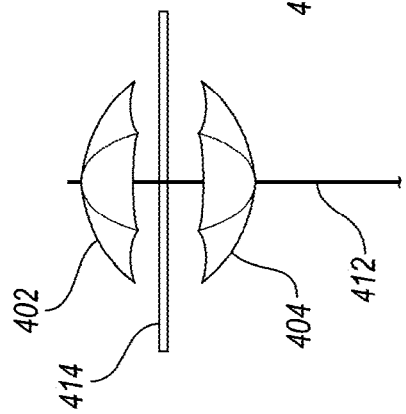
Figure 11A:
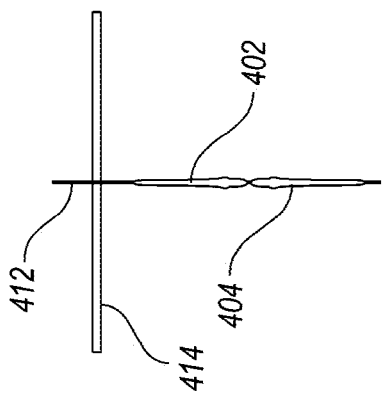

FIGS. 11A through 11D depict schematic, side views of an in-situ fenestration procedure using a self-expanding umbrella pair. In FIG. 11A, guidewire 412 penetrates graft material 414 to make an initial fenestration in graft material 414. First and second self-expanding umbrellas 402 and 404 are in a compressed, crimped state and covered by a capsule for delivery by in-situ fenestration device 400 along guidewire 412. First self-expanding umbrella 402 passes through the initial fenestration in the compressed, crimped state. Once first self-expanding umbrella 402 in the compressed, crimped state is on a first side of graft material 414 and second self-expanding umbrella 404 in the compressed, crimped state is on a second side of graft material 414, first and second self-expanding umbrellas 402 and 404 are expanded into an expanded state as shown in FIG. 11B. In one embodiment, first self-expanding umbrella 402 may be partially expanded by partially removing the capsule so that the tip of first self-expanding umbrella 402 punctures graft material 414 to advance through graft material 414. Once first self-expanding umbrella 402 advances through graft material 414, the capsule may be retracted to remove it from first self-expanding umbrella 402 and second self-expanding umbrella 404 so that umbrellas 402 and 404 are in the expanded state.

As shown in FIG. 11C, first self-expanding umbrella 402 and second self-expanding umbrella 404 in the expanded state are brought together so that umbrellas 402 and 404 contact graft material 414. At this point in the procedure, RF energy is applied to create fenestration 416 shown in FIG. 11D. While this embodiment describes RF ablation, any suitable energy-based cutting mechanism, such as a resistive heating element, may be used. After fenestration 416 is created, the capsule is advanced to transition umbrellas 402 and 404 from the expanded state to the compressed, crimped state, thereby also capturing any fenestration remnant therein. First self-expanding umbrella 402 may be inverted during the recapture step, however, any graft material or other embolic material may be trapped between the two umbrellas. At this point in the procedure, in-situ fenestration device 400 may be removed from the patient's vasculature, along with any trapped embolic material.

The in-situ fenestration device of one or more embodiments may have one or more of the following benefits. The in-situ fenestration device may create multiple fenestrations during a single procedure. In one or more embodiments, RF energy is not applied until proper alignment is achieved to prevent damage to the stent graft. The self-expanding umbrella frame may be woven of a durable fabric material and configured to contain graft material and procedural byproducts, thereby atraumatically removing byproducts generated from the procedure. Radiopaque (RO) markers disposed on the peripheral edge of the umbrellas may be used to assist alignment of the device, thereby avoiding or reducing the risk of damaging struts or sutures on the stent graft. The in-situ fenestration device may be capable of reliable and repeatable creation of fenestrations.

In one or more embodiments, an in-situ fenestration device with a protective member or backboard is disclosed. The in-situ fenestration device includes an outer catheter, an inner catheter, an electrode ring, and a backboard. The electrode ring is configured to create a fenestration in a graft material when the electrode ring is energized. The backboard is configured to protect the anatomy adjacent the fenestration site. The electrode ring may be included on the outer catheter. The backboard may be included on the inner catheter.

Figure 12B:
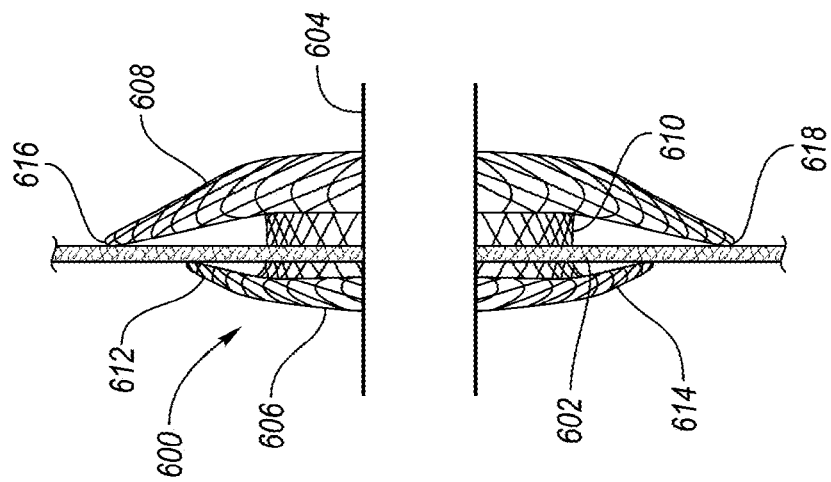
FIG. 12B depicts a schematic, side view of a button formed onto (e.g., integrated into) a fenestration made in the graft material of the stent graft shown in FIG. 12A.
Figure 12A:
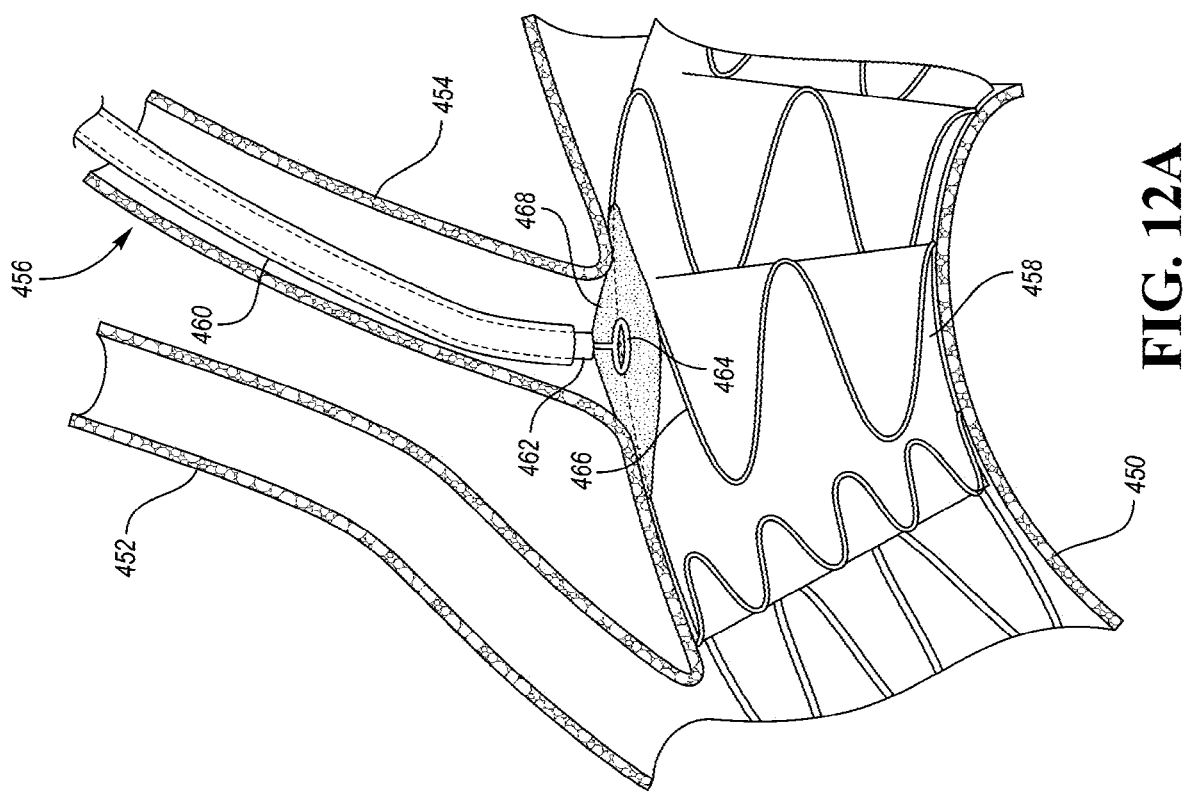
FIG. 12A depicts a partially cut away, schematic side view of an aortic arch branching into left common carotid artery and left subclavian artery, where an in-situ fenestration device accesses a fenestration site on a stent graft from the left subclavian artery.

FIG. 12A depicts a partially cut away, schematic side view of aortic arch 450 branching into left common carotid artery 452 and left subclavian artery 454. In-situ fenestration device 456 accesses a fenestration site on stent graft 458 from left subclavian artery 454. In-situ fenestration device includes outer catheter 460, inner catheter 462, electrode ring 464 attached to a distal portion of inner catheter 462, backboard 466 in a deployed position, and insulating component 468 in a deployed position. Backboard 466 may be formed of shape memory material (e.g., Nitinol) frame and a polymeric material (e.g., polytetrafluoroethylene (PTFE)) covering. Insulating component 468 may be formed of a shape memory material (e.g., Nitinol) frame and a polymeric material (e.g., PTFE) covering. The polymeric material covering is configured to form a heat protection from electrode ring 464 during fenestration cutting. During deployment, and as shown in FIG. 12A, backboard 466 and insulating component 468 are both released and expanded so that they contact both the outer and inner walls of stent graft 458, thereby protecting the surrounding anatomy from the cutting operation. Electrode ring 464 may be a closed loop (e.g., circular) radio frequency (RF) electrode configured to cut a fenestration at a fenestration site. The circular RF electrode is configured to create a fenestration in one step, thereby mitigating the amount of time that the RF electrode is activated. In the deployed position, electrode ring 464 is situated between backboard 466 and insulating component 468 to create a debris collection mechanism. The diameter of the circular RF electrode may be any of the following diameters or in a range of any two of the following diameters: 3, 4, 5, 6, and 7 millimeters. While electrode ring 464 is described in this embodiment as an RF ablation element, it may also be any suitable energy-based cutting mechanism, such as resistive heating element.

In one or more embodiments, a relatively small blade may be used to make an initial incision in a stent graft. The initial incision may be formed with a sharpened or pointed tip such that it can cut through graft material without electrification. In another embodiment, the tip may be vibrated at a high frequency (e.g., ultrasonic) to help it pierce the graft material.

Once the initial incision is made, backboard 466 may be advanced inside of stent graft 458. Backboard 466, which may be made from a self-expanding shape memory material, is configured to radially expand once released to include a stable surface for contact by electrode ring 464 for making a clean cut at a fenestration site. After backboard 466 has radially expanded within stent graft 458, backboard 458 is brought into contact with an inner wall of stent graft 458. Subsequently, electrode ring 464 is advanced until it contacts an outer wall of stent graft 458. Electrode ring 464 is then activated and creates a fenestration in stent graft 458 larger than the initial incision. The cooperation of electrode ring 464 and backboard 466 is configured to reduce or minimize fraying and/or tear propagation at the fenestration site. After the cutting operation, backboard 466 is then inverted and retracted back into outer catheter 460, thereby removing loose stent material to mitigate embolism risk. In one or more embodiments, once the fenestration cut is completed, backboard 466 or a balloon may be used to increase the size of the fenestration and/or to move one or more stent struts of stent graft 458. Insulating material 468, e.g., a heat resistant plastic (e.g., PTFE), may be used to reduce or minimize anatomical damage. Different sized outer and inner catheters and electrode rings may be used to achieve different sized cuts for different applications.

Figure 13C:
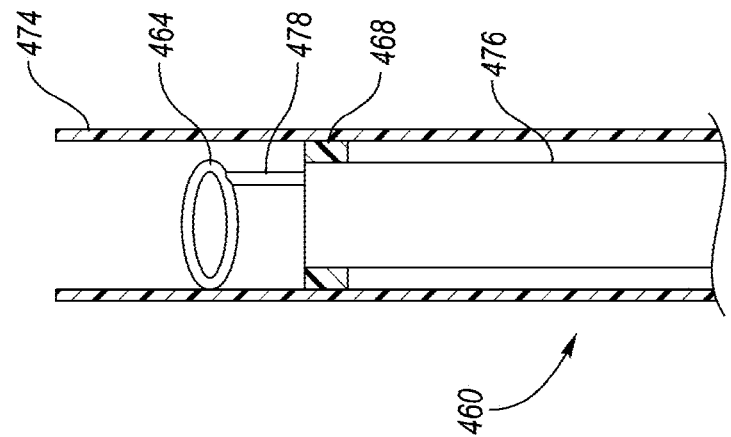
FIG. 13C depicts a cut away, schematic, isolated, side view of the outer catheter.
Figure 13B:
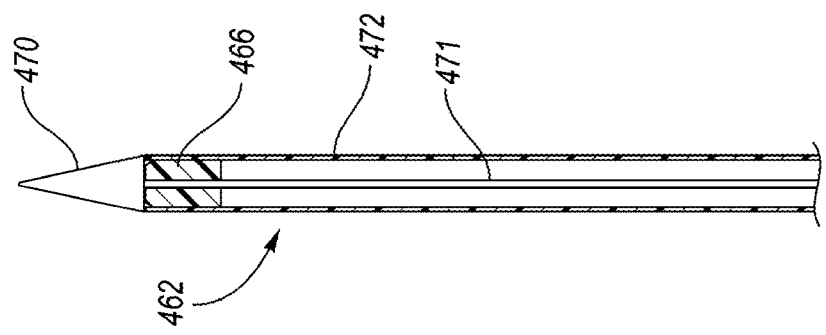
FIG. 13B depicts a cut away, schematic, isolated, side view of the inner catheter.
Figure 13A:
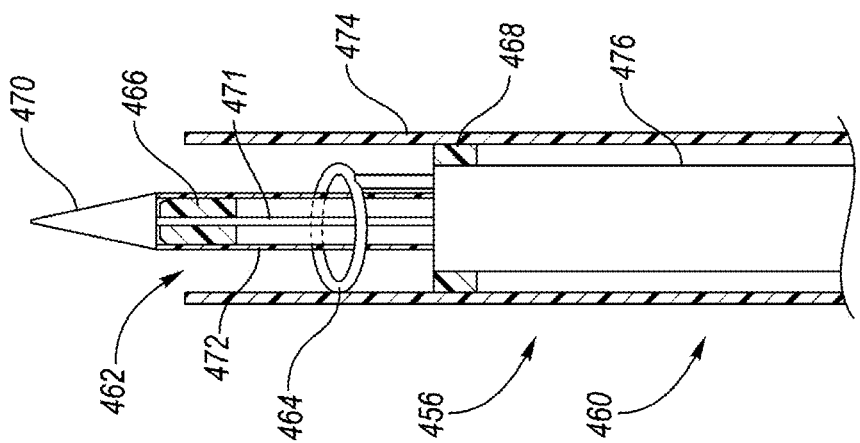
FIG. 13A depicts a cut away, schematic, side view of a distal portion of the in-situ fenestration device including an outer catheter and an inner catheter configured to track through the lumen of the outer catheter.

FIG. 13A depicts a cut away, schematic, side view of a distal portion of in-situ fenestration device 456 including outer catheter 460 and inner catheter 462 configured to track through the lumen of outer catheter 460. FIG. 13B depicts a cut away, schematic, isolated, side view of inner catheter 462. FIG. 13C depicts a cut away, schematic, isolated, side view of outer catheter 460.

As shown in FIGS. 13A and 13B, inner catheter 462 includes tip assembly 470 configured to puncture graft material of stent graft 458 and/or provide a tapered, atraumatic leading edge to the catheter. Tip assembly is mechanically connected to inner shaft 471. Inner catheter 462 also includes backboard 466 shown in FIGS. 13A and 13B in a constrained state. Inner sheath 472 of inner catheter 462 is retractable from an advanced position to a retracted position to release the backboard 466 to an unconstrained state.

As shown in FIGS. 13A and 13C, outer catheter 460 includes outer sheath 474, electrode ring 464, and inner shaft 476. Electrode ring 464 and inner shaft 476 are electrically connected to each other through wire 478. Inner shaft 476 houses wiring connected to wire 478. The wiring may be configured to supply radio frequency (RF) power to electrode ring 464. Insulating component 468 is shown situated within outer sheath 474 in a constrained state. Inner shaft 476 is configured to extend through insulating component 468.

Figure 14A:
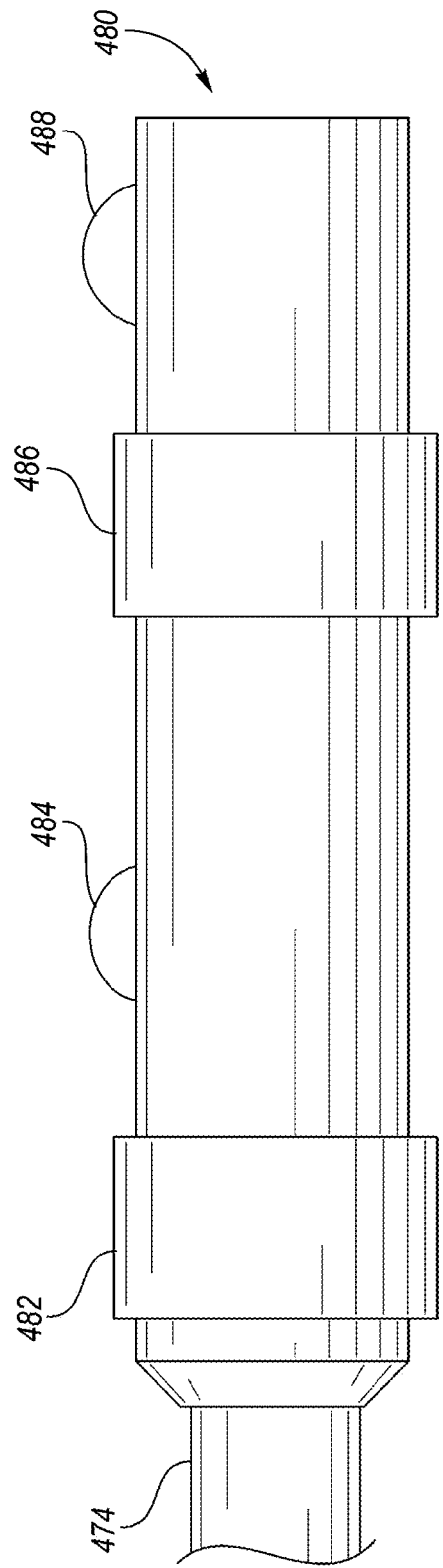
FIG. 14A depicts a schematic top view of proximal, handle assembly 480 of the in-situ fenestration device according to one embodiment.
Figure 14B:
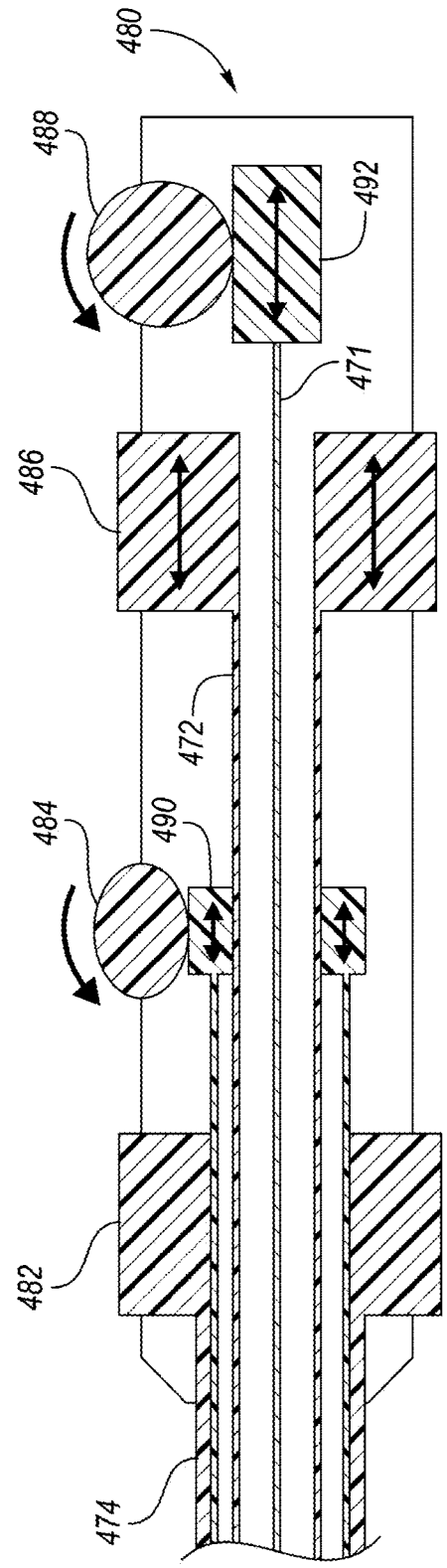
FIG. 14B depicts a schematic, cross section view of proximal, handle assembly of the in-situ fenestration device of FIG. 14A.

FIG. 14A depicts a schematic top view of proximal, handle assembly 480 of in-situ fenestration device 456. FIG. 14B depicts a schematic, cross section view of proximal, handle assembly 480 of in-situ fenestration device 456. As shown in FIGS. 14A and 14B, outer sheath 474 of outer catheter 460 is connected to handle assembly 480.

Handle assembly 480 includes outer sheath actuator 482, cutter assembly knob 484, inner sheath actuator 486, and tip actuator knob 488. Outer sheath actuator 482 is configured to slide linearly in distal and proximal directions to respectively advance and retract outer sheath 474. Cutter assembly knob 484 is configured to rotate in clockwise and counterclockwise directions to actuate slider 490, which is configured to slide linearly in distal and proximal directions to respectively advance and retract inner shaft 476 connected to electrode ring 464. Inner sheath actuator 486 is configured to slide linearly in distal and proximal directions to respectively advance and retract inner sheath 472. Tip actuator knob 488 is configured to rotate in clockwise and counterclockwise directions to actuate slider 492, which is configured to slide linearly in distal and proximal directions to respectively advance and retract inner shaft 471 connected to tip assembly 470.

Figure 15B:
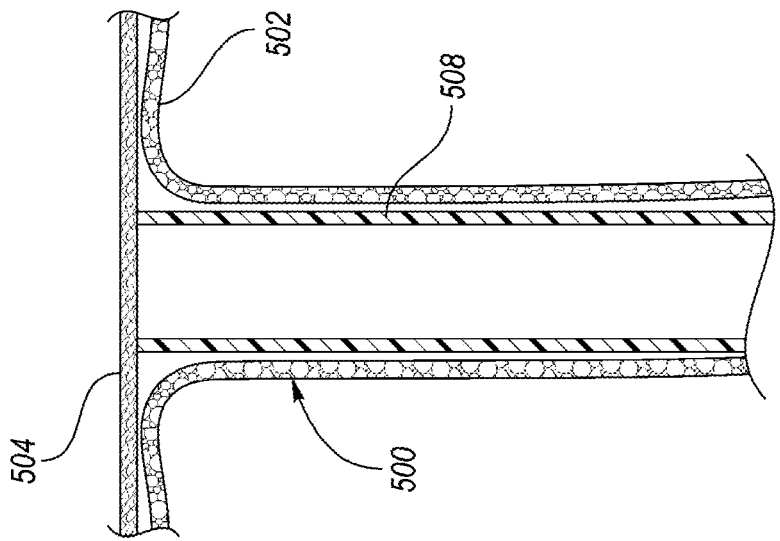
FIG. 15B depicts a schematic, cross section view of a guide catheter steered into a lumen and contacting the stent graft of FIG. 15A at a fenestration site.
Figure 15A:
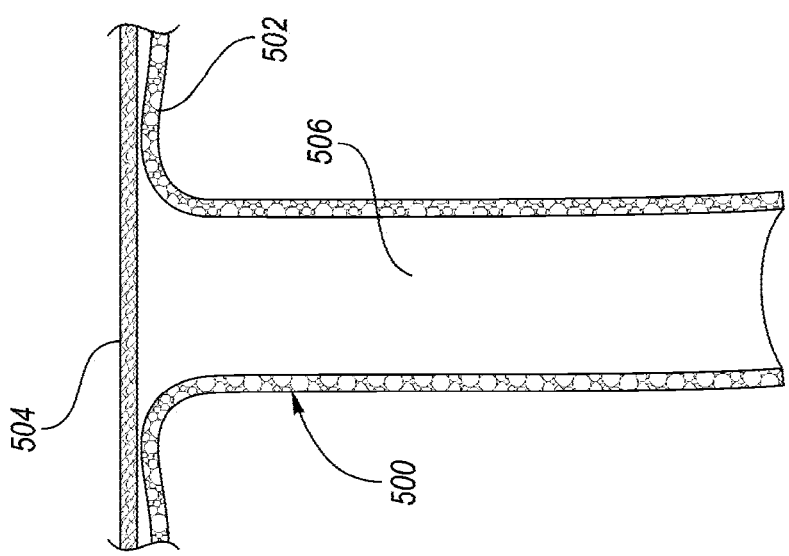
FIG. 15A depicts a schematic, cross section view of a side branch artery (e.g., brachiocephalic artery, left common carotid artery, or left subclavian artery) branching into an aortic arch where a stent graft is situated.

FIG. 15A depicts a schematic, cross section view of side branch artery 500 (e.g., brachiocephalic artery, left common carotid artery, or left subclavian artery) branching into aortic arch 502 where stent graft 504 is situated. Branch artery 500 includes lumen 506. FIG. 15B depicts a schematic, cross section view of guide catheter 508 steered into lumen 506 and contacting stent graft 504 at a fenestration site.

Figure 16D:
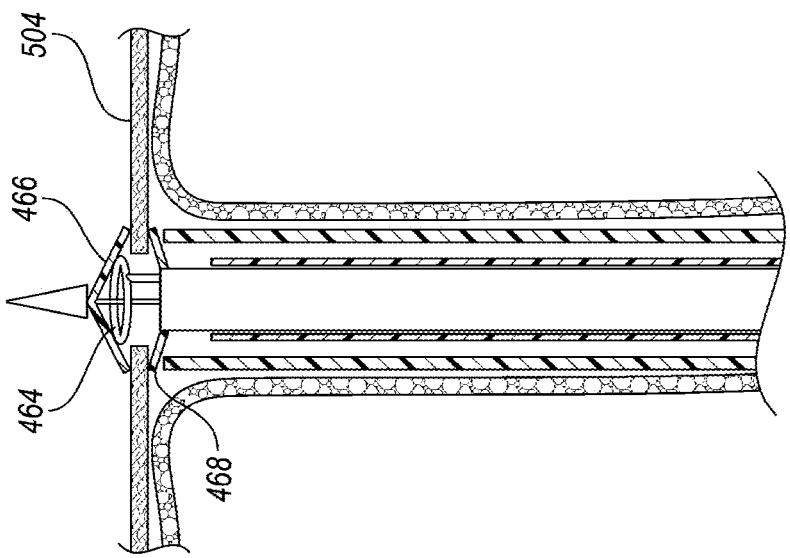

FIGS. 16A through 16H depict the procedural steps of in-situ fenestration device 456 forming a fenestration in the graft material of stent graft 504 according to one embodiment. In FIG. 16A, in-situ fenestration device 456, including outer catheter 460 and inner catheter 462, are tracked through guide catheter 508. Inner sheath 472 is advanced via inner sheath actuator 468, thereby piercing and pushing tip assembly 470 through the graft material of stent graft 504. As shown in FIG. 16B, inner sheath 472 is advanced through the graft material of stent graft 504 such that tip assembly 470 and backboard 466 in a constrained state within inner sheath 472 are situated within stent graft 504. A fluoroscopic band may be included on inner sheath 472 to guide the clinician to an optimal position. The position of tip assembly 470 may be adjusted via tip actuator knob 488.

Figure 16C:
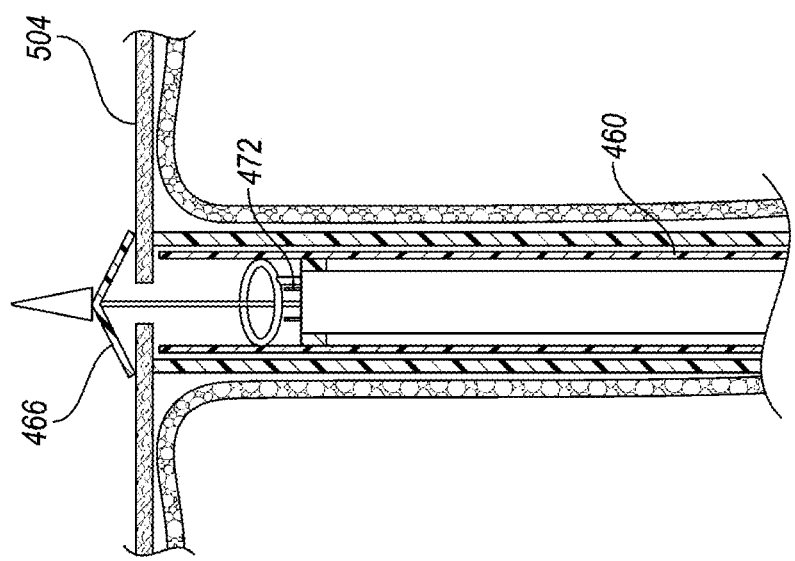

As shown in FIG. 16C, inner sheath 472 is retracted into the lumen of outer catheter 460, thereby transitioning backboard 466 into an unconstrained position within stent graft 504. As shown in FIG. 16D, electrode ring 464 is advanced up to the graft material of stent graft 504 via cutter assembly knob 484, thereby transitioning insulating component 468 into an exposed, unconstrained position. Electrode ring 464 is advanced up to backboard 466 via cutter assembly knob 484 and is configured to create a fenestration in the graft material at the fenestration site.

Figure 16F:
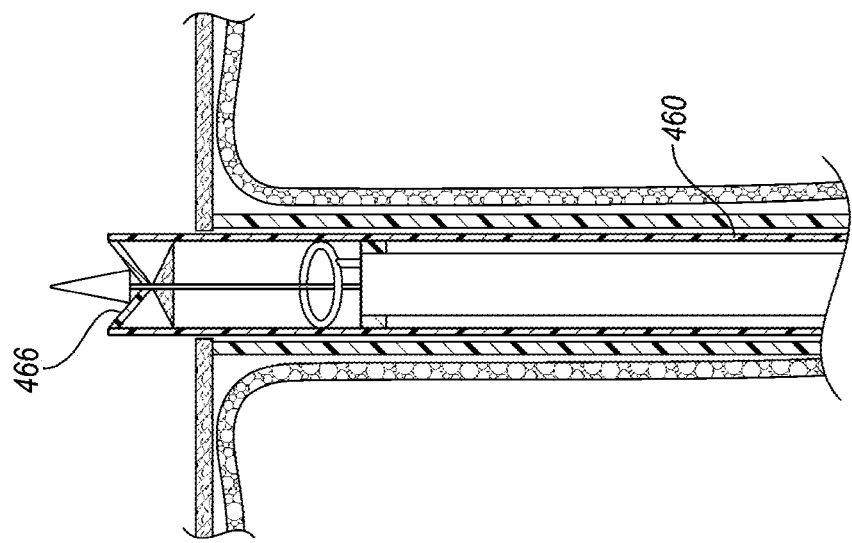
Figure 16E:
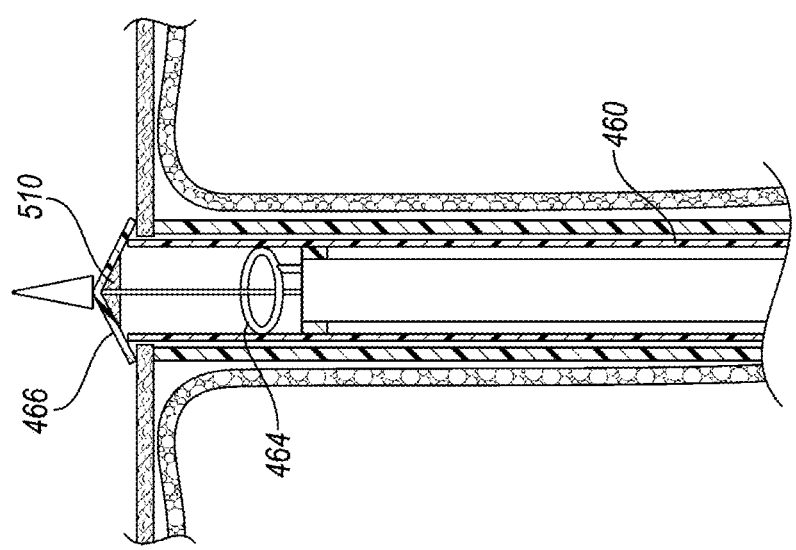

As shown in FIG. 16E, cut material 510 from the graft material is contained within the inner cavity formed by backboard 466, and electrode ring 464 is retracted into inner catheter 462 via cutter assembly knob 484. As shown in FIG. 16F, outer catheter 460 is advanced through the fenestration via outer sheath actuator 482, thereby inverting backboard 466 into an inverted position within outer catheter 460 and capturing cut material within outer catheter 460.

Figure 16G:
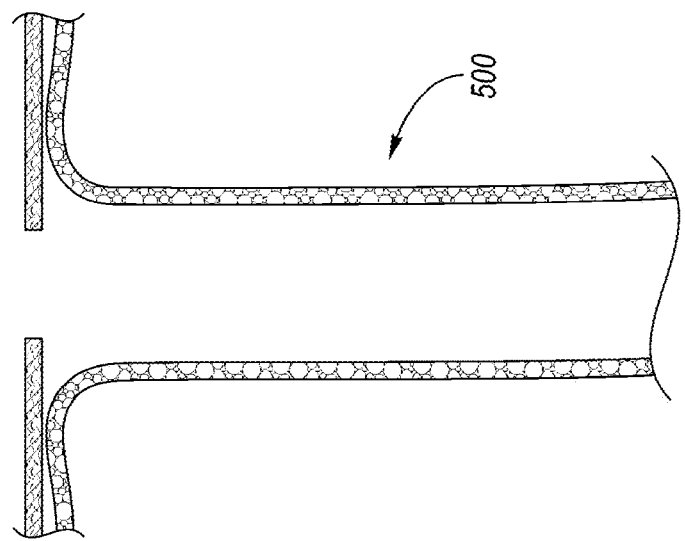
Figure 16H:
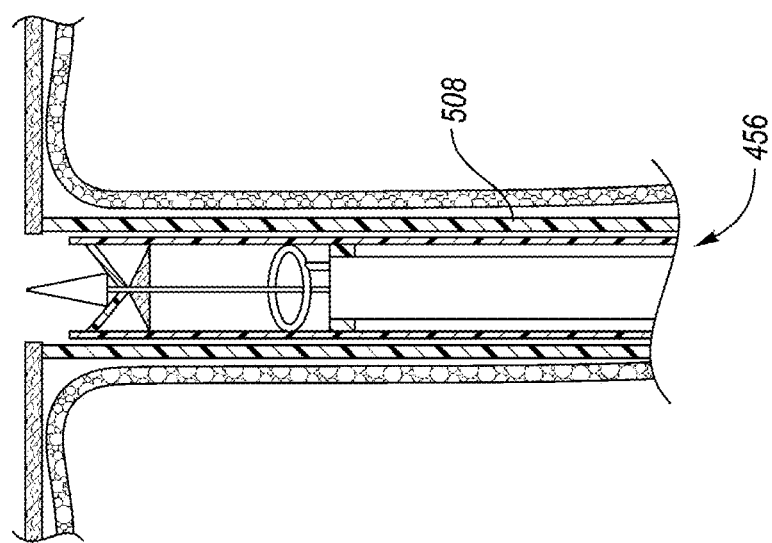

As shown in FIG. 16G, in-situ fenestration device 456 is retracted back through steerable guide catheter 508 and then removed from the patient's vasculature (including branch artery 500) as shown in FIG. 16H.

FIG. 17A depicts a schematic, side view of backboard 466 in a deployed, unconstrained position. FIG. 17B depicts an isolated view of center portion 550 of backboard 466. FIG. 17C depicts a schematic, side view of backboard 466 in an inverted position for removing in-situ fenestration device 456 from a patient's vasculature. In one or more embodiments, center portion 550 of backboard 466 has a window density (e.g., open area) less than the window density of the peripheral portion 552 of backboard 466. The lower window density provides increased density of the frame (e.g., Nitinol material) configured to provide a relatively stiffer area for the cutting operation. The material covering the frame may also add additional reinforcement for the cutting operation. In one or more embodiments, peripheral portion 552 of backboard 466 has a relatively larger window density and/or a thinner layer of covering material configured to be more flexible than center portion 550 to aid in the inversion of backboard 466. In one or more embodiments, guide catheter 508 has a greater column strength than electrode ring 464 to aid in the inversion of backboard 466.

FIG. 12B depicts a schematic, side view of grommet or button 600 formed onto (e.g., integrated into) a fenestration made in graft material 602. Button 600 defines channel 604 configured to house a portion of a branching stent (not shown). Button 600 includes inner portion 606 (e.g., a portion inside graft material 602), outer portion 608 (e.g., a portion outside graft material 602), and middle portion 610 extending between inner portion 606 and outer portion 608. As shown in FIG. 12B, inner portion 606 includes first and second edges 612 and 614 and outer portion 608 includes first and second edges 616 and 618. First edges 612 and 616 may be configured to clamp graft material 602. Second edges 614 and 618 may be configured to clamp graft material 602. Button 600 may be configured to clamp and/or to contain any frayed cut edges of the fenestration made in graft material 602. Button 600 may be configured to restrict propagation of tears and/or rips in graft material 602 at the fenestration and to provide a lumen of covered stent expansion.

Figure 18A:
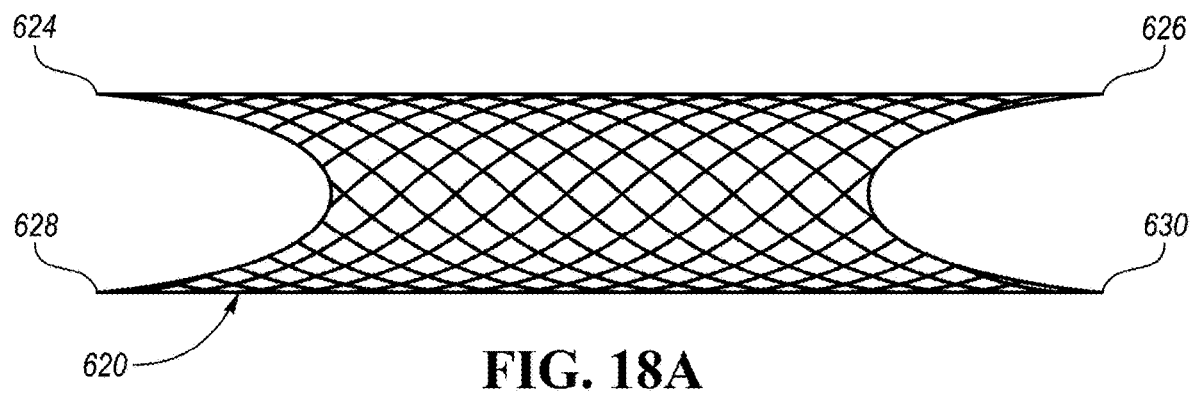
FIGS. 18A, 18B, and 18C depict side views of an outer stent, an inner stent, and the outer and inner stents combined to form a button.
Figure 18B:
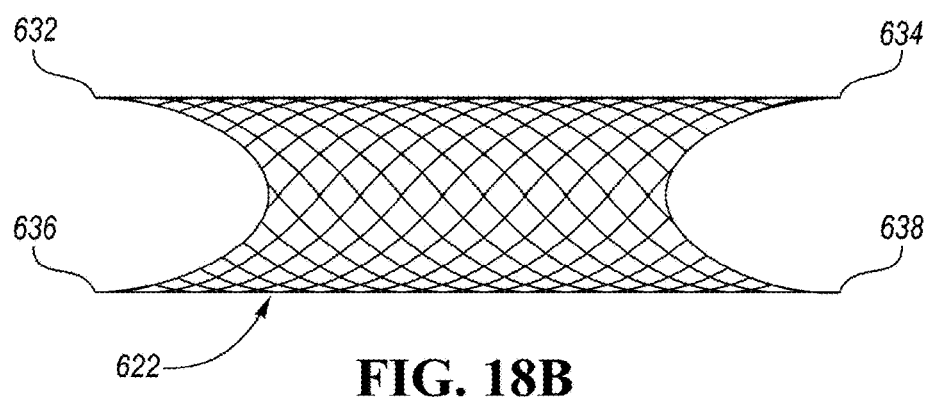
Figure 18C:
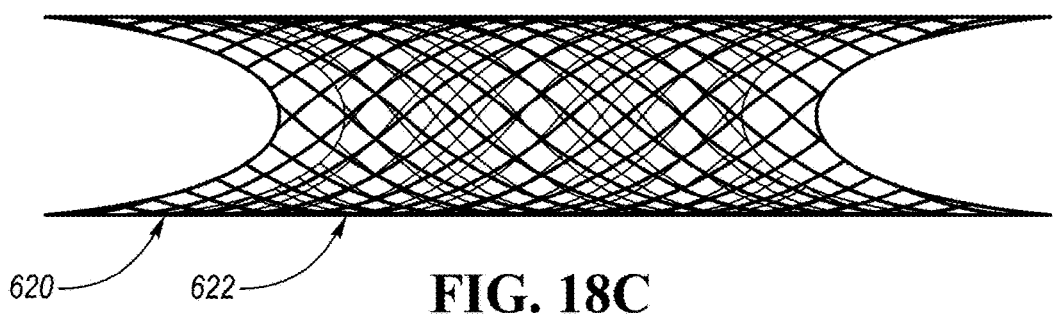
Figure 18D:
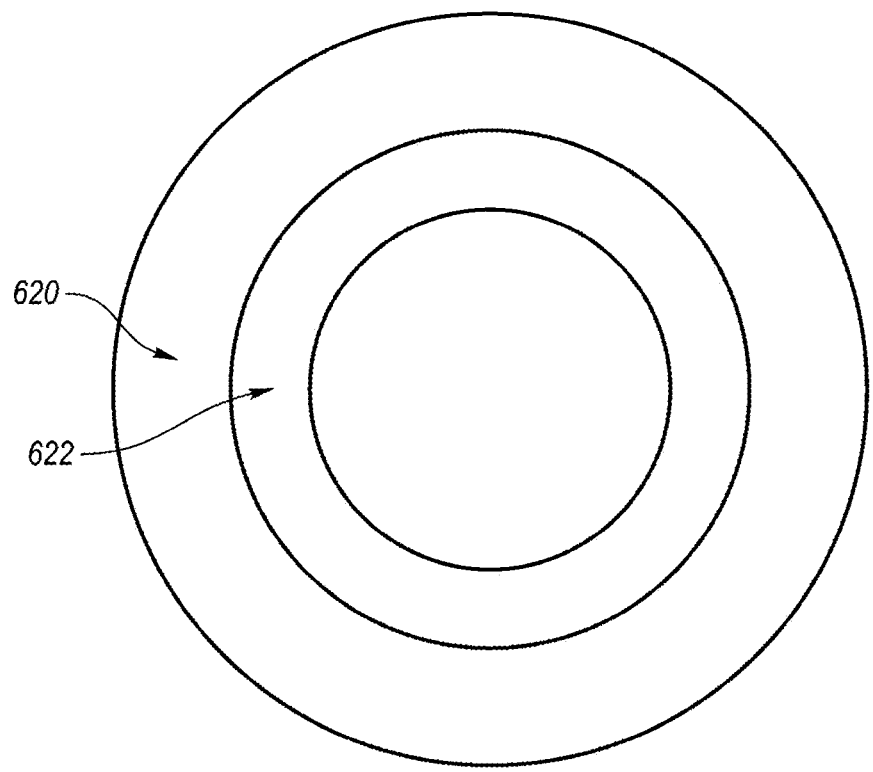
FIG. 18D depicts a plan view of outer stent and inner stent combined.

FIGS. 18A, 18B, and 18C depict side views of outer stent 620, inner stent 622, and outer stent 620 and inner stent 622 combined to form a button, respectively. FIG. 18D depicts a plan view of outer stent 620 and inner stent 622 combined. Outer stent 620 and inner stent 622 may collectively form button 600. Outer stent 620 includes upper edges 624 and 626 and lower edges 628 and 630. Inner stent 622 includes upper edges 632 and 634 and lower edges 636 and 638. As shown in FIG. 18C, inner stent 622 is located within outer stent 620. In another embodiment, a portion of outer stent 620 may be located within inner stent 622. The stent wires of the inner and outer stents 622 and 620 may be fastened to each other with crimping or other fastening mechanism. Inner and outer stents 622 and 620 may be formed of a shape memory material such as a Nitinol wire material.

FIGS. 19A through 19E depict partially cut away, schematic side views of procedural steps for deploying button 650 into fenestration 652 in graft material 651. Fenestration 652 is configured to create a pathway for the flow of blood from aortic arch 653 to branch vessel 655.

Figure 19B:
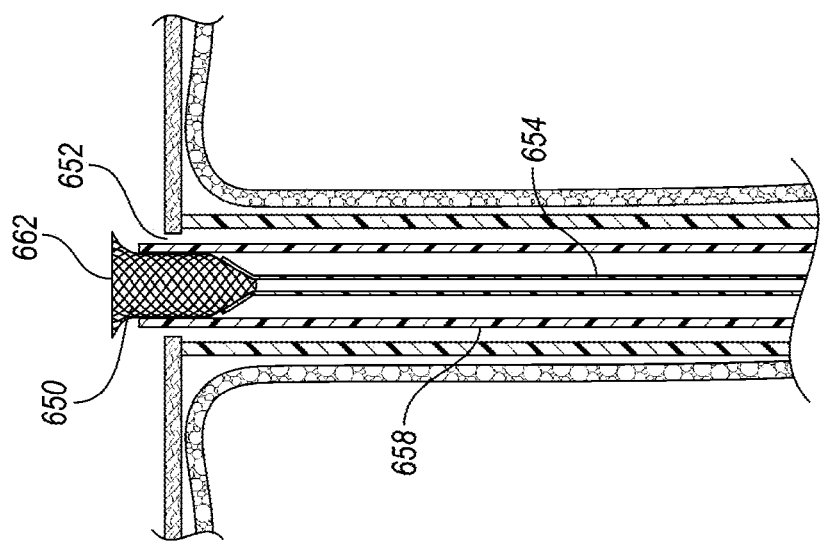
Figure 19A:
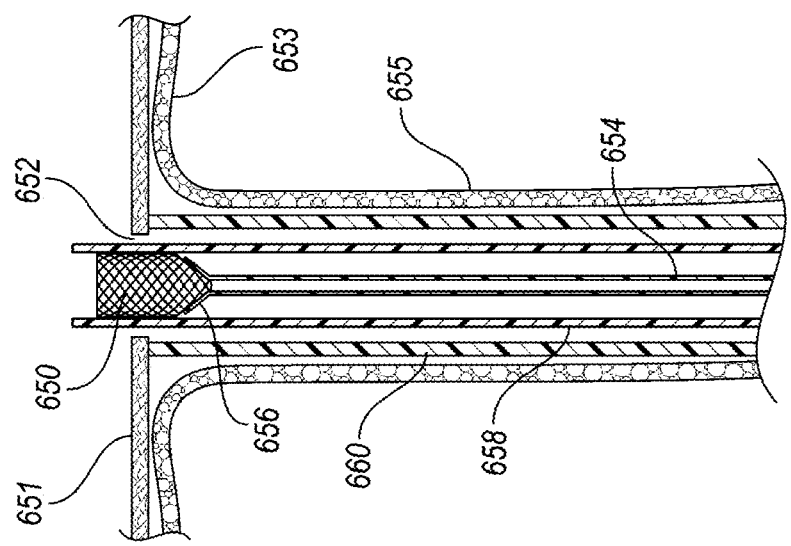

As shown in FIG. 19A, button delivery system 654 includes inner support member 656 (e.g., inner supporting cone as shown in FIG. 19A) configured to partially support button 650 in a delivery position. Button delivery system 654 and button 650 are delivered to fenestration 652 in sheath 658 through branch vessel 655, where these components collectively advance through guide catheter 660.

As shown in FIG. 19B, sheath 658 is retracted relative to button delivery system 654 to initiate deployment of button 650. During this operation, the proper positioning of button 650 within fenestration 652 may be checked. As shown in FIG. 19B, distal end 662 of button 650 is released from sheath 658.

As shown in FIG. 19C, button delivery system 654 and sheath 658 are collectively retracted within guide catheter 660 so that distal end 662 of button 650 seats against graft material 651 on the internal face thereof.

As shown in FIG. 19D, guide catheter 660 and sheath 658 are retracted to prepare for final deployment of button 650. During this operation, button 650 is connected to inner support member 656.

As shown in FIG. 19E, inner support member 656 is retracted within sheath 658 to fully deploy button 650. In the deployed position, proximal end 664 of button 650 seats against graft material 651 on the external face thereof.

Figure 20B:
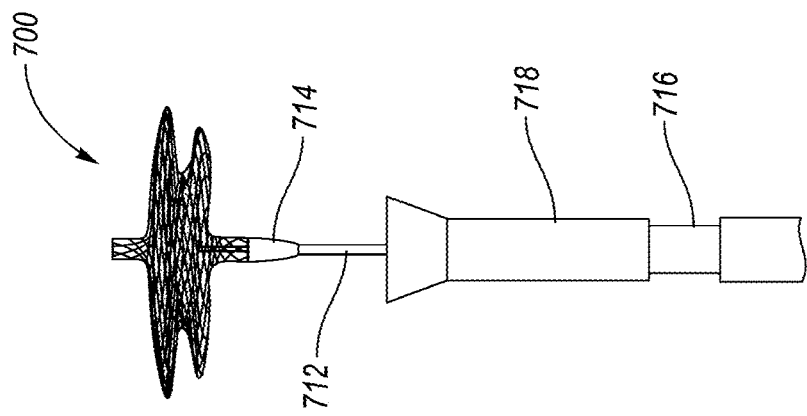
FIGS. 20A and 20B depict side views of a button in a delivery position and a deployment position, respectively.
Figure 20A:
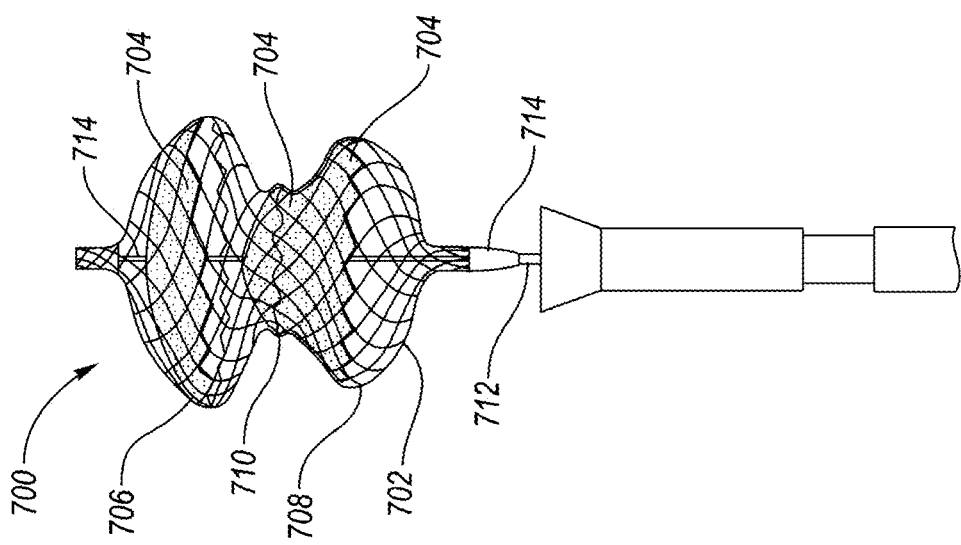

FIGS. 20A and 20B depict side views of button 700 in a delivery position and a deployment position, respectively. In one or more embodiments, button 700 includes a central channel extending therethrough and configured to receive a secondary stent graft. In such embodiments, upon deployment of button 700, upper and lower openings (not shown) are defined in button 700 such that button 700 is configured to receive the secondary stent graft. For instance, the upper and lower pointed portions shown in FIGS. 20A and 20B are converted into openings during deployment of button 700. As shown in FIG. 20A, button 700 includes stent material 702 and membrane material 704 located within stent material 702. Membrane material 704 may be a biodegradable membrane material (e.g., poly (l-lactic) acid (PLLA)). Button 700 includes distal portion 706, proximal portion 708, and medial portion 710 extending between distal portion 706 and proximal portion 708. Membrane material 704 may be included within stent material 702 of distal portion 706, proximal portion 708, and medial portion 710. Button 700 is connected to cable 712, which has a locking system 714 configured to lock cable 712 to button 700 in the delivery position. Cable includes screw 714 configured to connect to proximal portion 708. The delivery system for button 700 includes loader 716 and subloader 718 collectively configured to aid in deployment of button 700 in the deployed position as shown in FIG. 20B.

A button of one or more embodiments may have one or more of the following benefits. The button may be deployed using mechanical means to eliminate heat damage risk. The button may be deployed using a single, retrograde approach. The button may provide a predictable and/or robust conduit diameter for a secondary branching stent. The hollow button may be compatible with encapsulation of shape memory struts (e.g., Nitinol struts). The hollow button may reinforce the fenestration to prevent or resist fraying or tearing of the graft material when a branch stent graft is deployed therein.

In one or more embodiments, surface modulation may be used as pre-fenestration step for changing material conditions of a fenestration site. The surface modulation of one or more embodiments may be applied before the backboard cutting operation and/or button delivery operation. In one or more embodiments, the surface modulation modifies the morphology of the graft material to reduce the amount of material fraying or tearing during fenestration. In one embodiment, a heat treatment may be applied to a fenestration zone. In another embodiment, an adhesive patch or layer may be applied to a fenestration zone. A fluoroscopic patch may be used to create a landing zone for an in-situ fenestration device.

In one embodiment, an in-vivo heat treatment of graft material may be done prior to fenestration. The fenestration site may be heated at retrograde or antegrade position with ablation or microwave technology (e.g., DiamondTemp Ablation catheter or Emprint Ablation System, both available from Medtronic PLC of Minneapolis, Minnesota). A device may be inserted with an attached heating element and positioned at a desired fenestration site. The heating element in the device is used to heat the desired fenestration site to a point where the material is near the glass transition temperature of the graft material without damaging the graft material or anatomy of the patient. Once a desired temperature has been reached and sufficient graft material has been modified, the user can continue with a fenestration procedure. The heat treatment may reduce or eliminate expansion and/or tearing of a fenestration made with an in-situ fenestration device.

Figure 21:
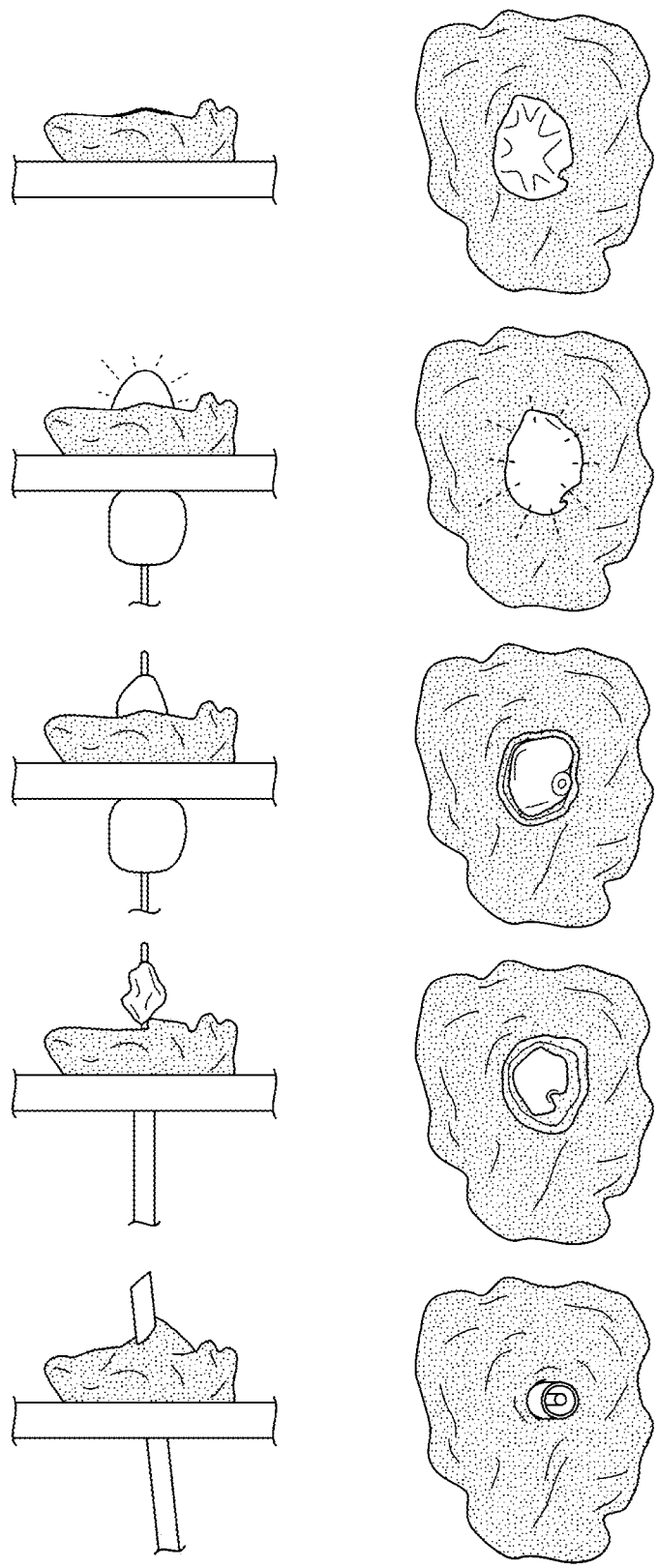
FIG. 21 depicts an example of applying an adhesive patch to an ulcer where the application process may also be used on stent material before an in-situ fenestration operation.
Figure 22C:
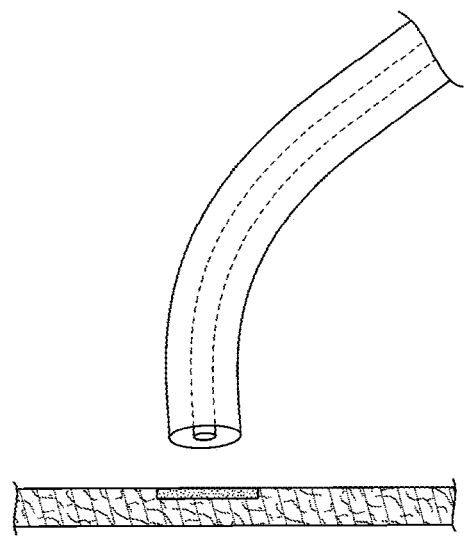
FIGS. 22A, 22B, and 22C depict schematic views for using a venaseal guide at a fenestration site to deploy an adhesive patch or layer onto the graft material at the fenestration site and to retract the venaseal guide after deployment.
Figure 22B:
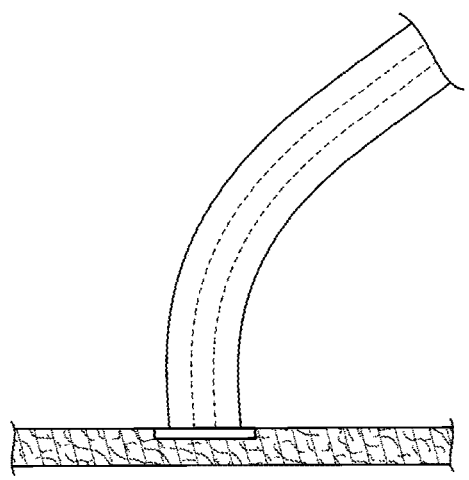
Figure 22A:
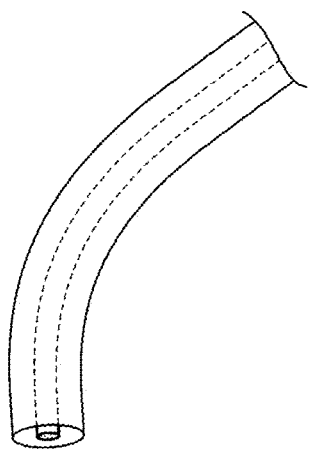

In another embodiment, an in-vivo adhesive layer may be applied to a graft material before in-situ fenestration to modify surface morphology. A device (e.g., a venaseal or custom device) may be inserted and positioned at a desired fenestration site. An adhesive layer or patch may be applied at the desired fenestration site. The heat treatment may reduce or eliminate expansion and/or tearing of a fenestration made with an in-situ fenestration device. FIG. 21 depicts an example of applying an adhesive patch to an ulcer where the application process may also be used on stent material before an in-situ fenestration operation. FIGS. 22A, 22B, and 22C depict schematic views for using a venaseal guide at a fenestration site to deploy an adhesive patch or layer onto the graft material at the fenestration site and to retract the venaseal guide after deployment.

FIGS. 23A, 23B, and 23C depict schematic views of an in-situ fenestration device in accordance with an embodiment where backboard 750 retrieves cut material when retracted.

Figure 24A:
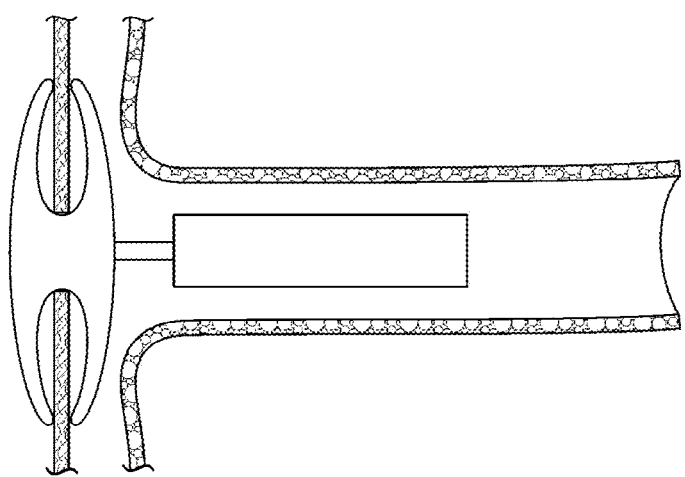
FIGS. 24A, 24B, and 24C depict schematic views of a deployment of a button to a fenestration using a retrograde approach where an aortic side is deployed first and seated, and the branch side second.
Figure 24B:
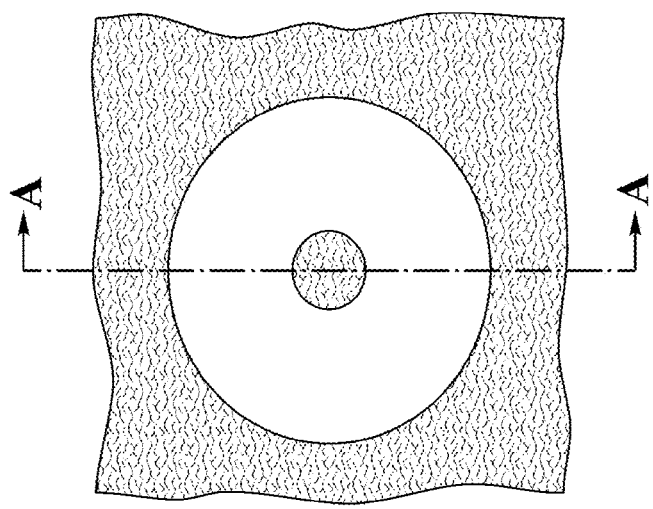
Figure 24C:
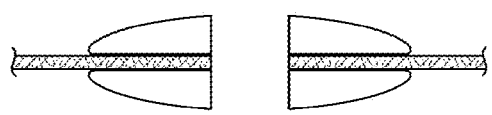
Figure 25B:
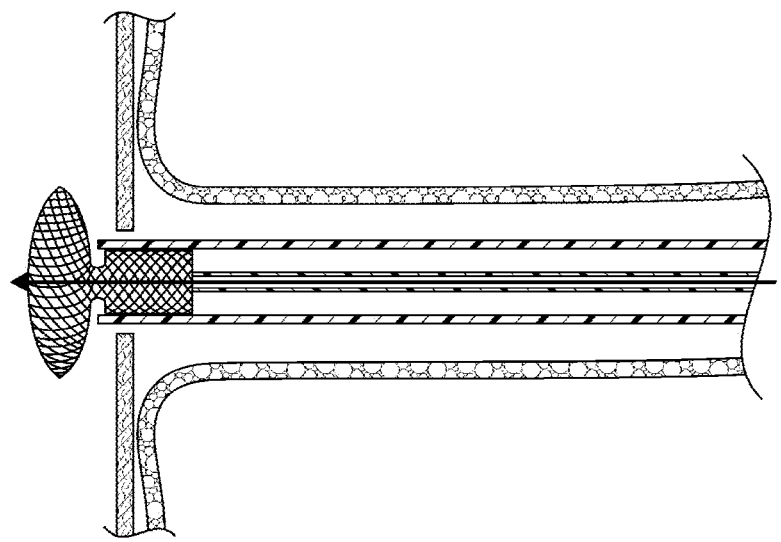
Figure 25A:
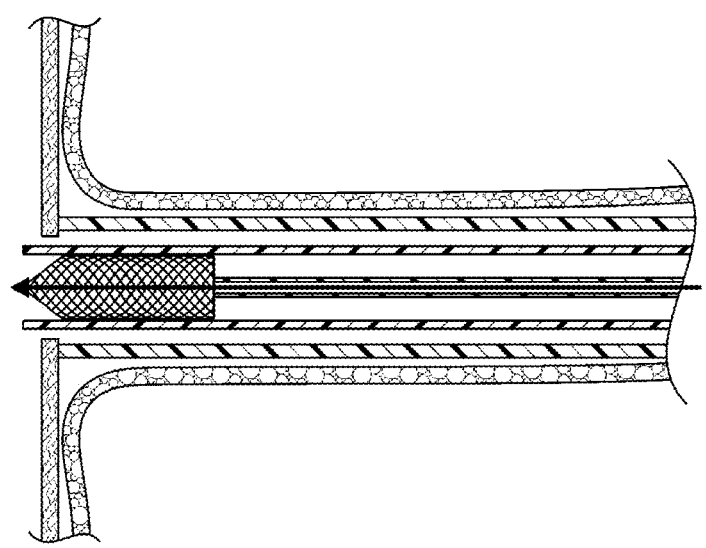
Figure 25D:
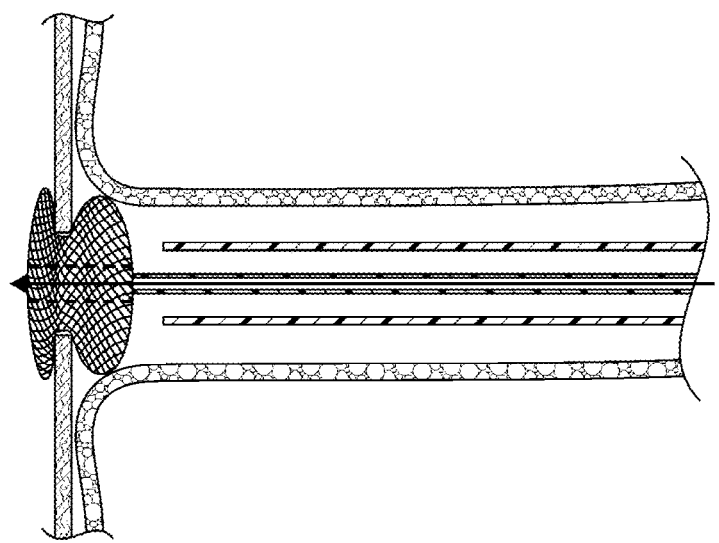
Figure 25C:
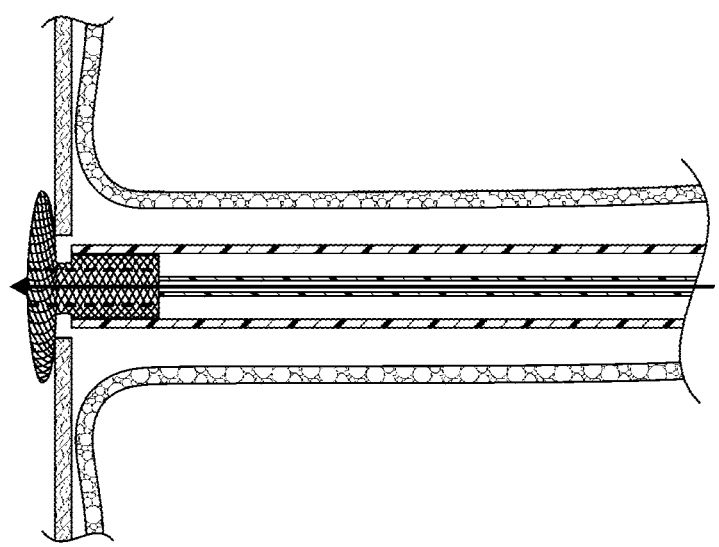

FIGS. 24A, 24B, and 24C depict schematic views of a deployment of a button to a fenestration using a retrograde approach where an aortic side is deployed first and seated, and the branch side second.

FIGS. 25A through 25G depict schematic views of a procedure for deploying the button shown in FIGS. 24A, 24B, and 24C.

The detailed description set forth herein includes several embodiments where each of the embodiments include several components, features, and/or steps. For the avoidance of doubt, any component, feature, and/or step of one embodiment may be applied, mixed, substituted, matched, and/or combined with one or more components, features, and/or steps of other embodiments. Such resulting embodiments are expressly within the scope of this disclosure. For example, any systems and methods for locating a branch ostium of a branch vessel disclosed herein may be used in conjunction with any disclosed embodiments. Similarly, any systems, methods, or energy types for creating a fenestration (e.g., heat, laser, vibration, RF energy, blades/mechanical cutting) may be used in any disclosed embodiments. In any of the embodiments disclosed herein, following the creation of a fenestration the fenestration may be reinforced or strengthened by placing a stent or grommet like device in the fenestration. After a fenestration is created (and optionally reinforced), a branch stent graft may be tracked and deployed within the fenestration using a separate delivery system. The branch stent graft may extend within the fenestration and at least partially within a main lumen of the fenestrated stent graft and into a branch artery (e.g., renal artery, celiac, SMA, BCA, LCC, LSA, etc.). The systems, methods, and devices disclosed herein may be used to make multiple fenestrations in a single stent graft, which thereafter each receive a branch stent graft.

While exemplary embodiments are described above, it is not intended that these embodiments describe all possible forms. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An in-situ fenestration device comprising:
   a sheath;
   a sonic catheter extending with the sheath and having a cutting tool at a distal section thereof; and
   a balloon catheter extending within the sonic catheter,
   the cutting tool of the sonic catheter configured to cut a fenestration in a graft material at a fenestration site of a stent graft upon being energized with ultrasonic energy at a cutting frequency.

2. The in-situ fenestration device of claim 1, wherein the balloon catheter is configured to capture the fenestration.

3. The in-situ fenestration device of claim 1 further comprising a sonic generator configured to energize the cutting element.

4. The in-situ fenestration device of claim 1, wherein the cutting frequency is 20 to 40 kHz.

5. The in-situ fenestration device of claim 1, wherein the cutting tool includes a proximal section and a distal section, the distal section of the cutting tool carrying a cutting element.

6. The in-situ fenestration device of claim 5, wherein the cutting tool tapers outward from the proximal section to the distal section to form a conical shape.

7. The in-situ fenestration device of claim 5, wherein the cutting element includes a circular saw tooth profile.

8. The in-situ fenestration device of claim 5, wherein the cutting element includes barbs.

9. The in-situ fenestration device of claim 8, wherein the barbs have angled edges.

10. The in-situ fenestration device of claim 8, wherein the barbs have angled edges including chamfers.

11. An in-situ fenestration device comprising:
    a sheath;
    a sonic catheter extending with the sheath and having a cutting tool at a distal section thereof;
    a balloon catheter extending within the sonic catheter; and
    a locating device carried on a distal end of a guidewire and configured to locate the fenestration site, and
    the cutting tool of the sonic catheter configured to cut a fenestration in a graft material at the fenestration site of a stent graft upon being energized with ultrasonic energy at a cutting frequency.

12. The in-situ fenestration device of claim 11, wherein the locating device includes a locator carried on a distal end thereof.

13. The in-situ fenestration device of claim 12, wherein the locator has a spiral profile.

14. The in-situ fenestration device of claim 12, wherein the locating device includes a balloon configured to expand the locator in a deployment state.

15. The in-situ fenestration device of claim 11, wherein the sheath is configured to extend over a sheath guidewire, the guidewire is the sheath guidewire.

16. A method of forming a fenestration in a graft material at a fenestration site of a stent graft, the method comprising:
   delivering a balloon of a balloon catheter to the fenestration site;
   locating a sonic cutting tool on a distal end of a sonic catheter at the fenestration site by inflating the balloon; and
   energizing the sonic cutting tool with ultrasonic energy at a cutting frequency to cut the fenestration in the graft material at the fenestration site of the stent graft.

17. The method of claim 16 further comprising advancing the sonic cutting tool toward the graft material until a resistance is sensed as the sonic cutting tool contacts an inner surface of the graft material.

18. The method of claim 16 further comprising advancing the sonic cutting tool external the stent graft during the energizing step.

19. The method of claim 16, wherein the energizing step forms a cut remnant of the graft material, and further comprising capturing the cut remnant by retracting the balloon.

20. The method of claim 16 further comprising deploying a grommet within the fenestration.

* * * * *